(12) United States Patent
Bailus et al.

(10) Patent No.: US 11,066,448 B2
(45) Date of Patent: Jul. 20, 2021

(54) ZIKA AS A CELL PENETRATING PEPTIDE FOR DELIVERY TO THE BRAIN

(71) Applicant: Buck Institute for Research on Aging, Novato, CA (US)

(72) Inventors: Barbara J. Bailus, Novato, CA (US); Lisa M. Ellerby, San Anselmo, CA (US)

(73) Assignee: Buck Institute for Research on Aging, Novato, CA (US)

( * ) Notice: Subject to any disclaimer, the term of this patent is extended or adjusted under 35 U.S.C. 154(b) by 0 days.

(21) Appl. No.: 16/405,745

(22) Filed: May 7, 2019

(65) Prior Publication Data

US 2019/0382451 A1    Dec. 19, 2019

Related U.S. Application Data

(60) Provisional application No. 62/670,609, filed on May 11, 2018.

(51) Int. Cl.
| | | |
|---|---|---|
| *A61K 47/42* | (2017.01) | |
| *A61K 47/64* | (2017.01) | |
| *A61K 47/65* | (2017.01) | |
| *C07K 14/18* | (2006.01) | |
| *C07K 19/00* | (2006.01) | |
| *C07K 14/01* | (2006.01) | |

(Continued)

(52) U.S. Cl.
CPC ............ *C07K 14/01* (2013.01); *A61K 9/0085* (2013.01); *A61K 47/42* (2013.01); *A61K 47/64* (2017.08); *A61K 47/65* (2017.08); *C07K 14/1825* (2013.01); *C12N 15/66* (2013.01); *A61K 38/00* (2013.01); *C07K 2319/33* (2013.01); *C07K 2319/43* (2013.01); *C07K 2319/50* (2013.01); *C07K 2319/74* (2013.01); *C07K 2319/80* (2013.01); *C12N 2310/20* (2017.05)

(58) Field of Classification Search
CPC ...... A61K 38/162; A61K 47/42; A61K 47/64; A61K 47/65; C07K 14/08; C07K 14/1825; C07K 2319/00; C07K 2319/10; C07K 2319/15
See application file for complete search history.

(56) References Cited

U.S. PATENT DOCUMENTS

2017/0312354 A1 * 11/2017 Paessler ................... C12N 7/00

FOREIGN PATENT DOCUMENTS

WO    WO-2018237313 A1 * 12/2018    ............... C12N 7/00

OTHER PUBLICATIONS

Cromwell et al. (2018) "Incorporation of bridged nucleic acids into CRISPR RNAs improves Cas9 endonuclease specificity" *Nat. Comm.* 9: 1448 [11 pages].

(Continued)

*Primary Examiner* — Jeffrey E. Russel
(74) *Attorney, Agent, or Firm* — Tom Hunter; Weaver Austin Villeneuve & Sampson LLP

(57) ABSTRACT

In various embodiments constructs are provided for the delivery of an effector molecule into a cell. In certain embodiments the construct comprises a cell penetrating peptide (CPP) attached to an effector that is to be delivered into a cell, where the cell penetrating peptide comprises a Zika cell penetrating peptide (Zika CPP), and the effector is selected from the group consisting of a protein, a nucleic acid, an organic compound, a nanoparticle, a viral particle, and the like.

25 Claims, 11 Drawing Sheets

Specification includes a Sequence Listing.

A

B

(51) Int. Cl.
    *C12N 15/66* (2006.01)
    *A61K 9/00* (2006.01)
    *A61K 38/00* (2006.01)

(56) References Cited

OTHER PUBLICATIONS

Rádis-Baptista (2017) "Cell-penetrating peptides (CPPs): From delivery of nucleic acids and antigens to transduction of engineered nucleases for application in transgenesis" *J. Biotechnol.* 252: 15-26.
Ramakrishna, et al. (2014) "Gene disruption by cell-penetrating peptide-mediated delivery of Cas9 protein and guide RNA" *Genome Res.*, 24(6): 1020-1027.
Sirohi et al. (2016) "The 3.8 Å resolution cryo-EM structure of Zika virus" *Science*, 352(6284): 467-470. DOI: 10.1126/science.aaf5316 [with Supplementary Materials (17 pages)].
Smit et al. (2011) "Flavivirus Cell Entry and Membrane Fusion" *Viruses*, 3(2): 160-171.
Suresh et al. (2017) "Cell-Penetrating Peptide-Mediated Delivery of Cas9 Protein and Guide RNA for Genome Editing" *Meth. Mol. Biol.* 1507: 81-94.
Tang et al. (2016) "Zika Virus Infects Human Cortical Neural Progenitors and Attenuates Their Growth" *Cell Stem Cell*, 18(5): 587-590.

\* cited by examiner

B
1d post-nuc BF    1d post-nuc EGFP
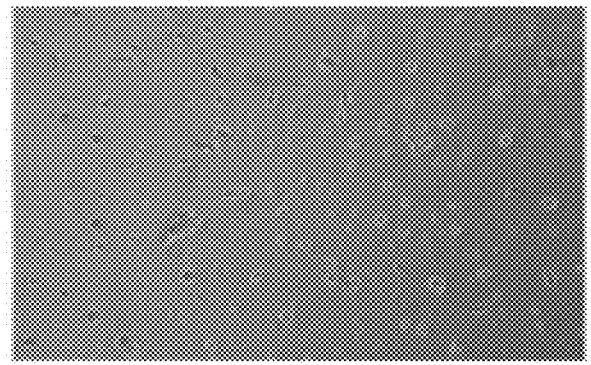
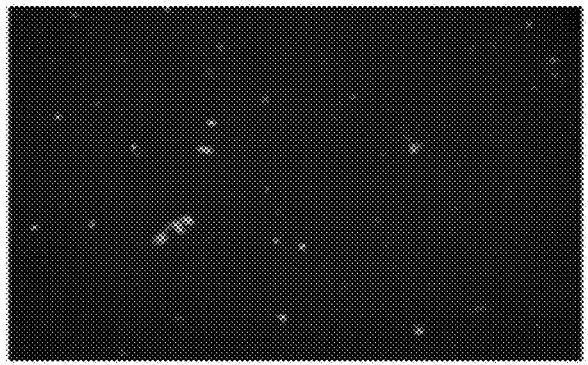
16 d G418 EGFP
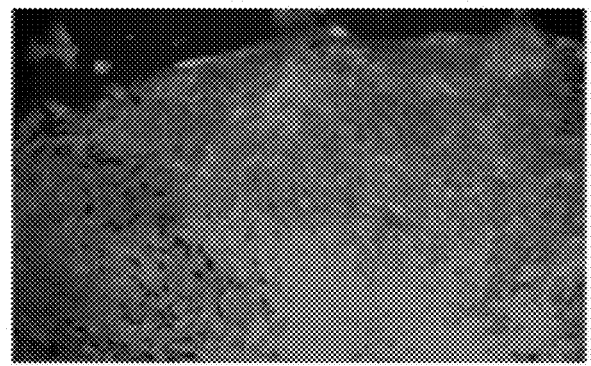
*Fig. 1, cont'd.*

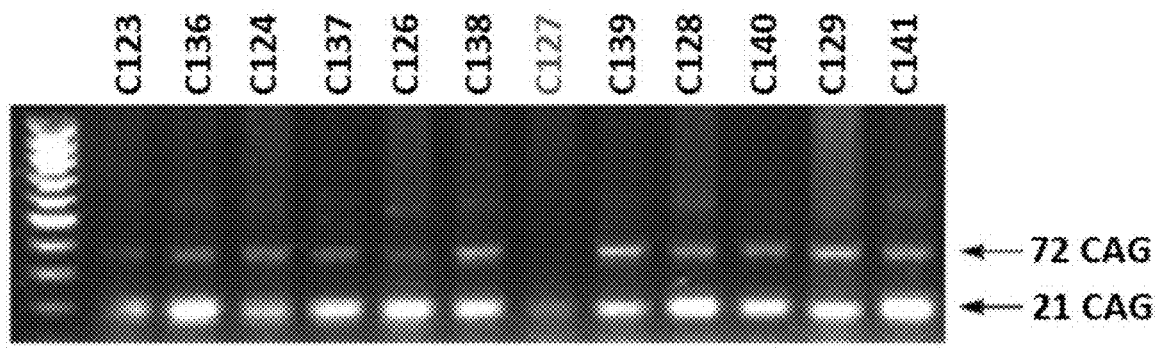
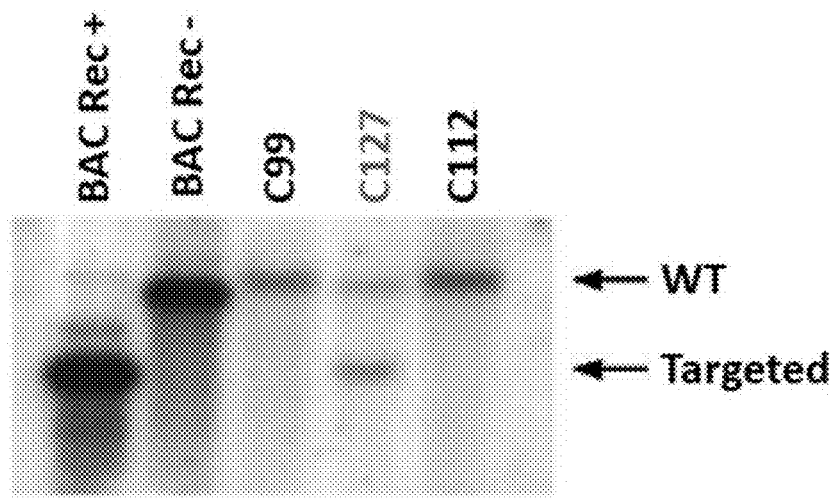
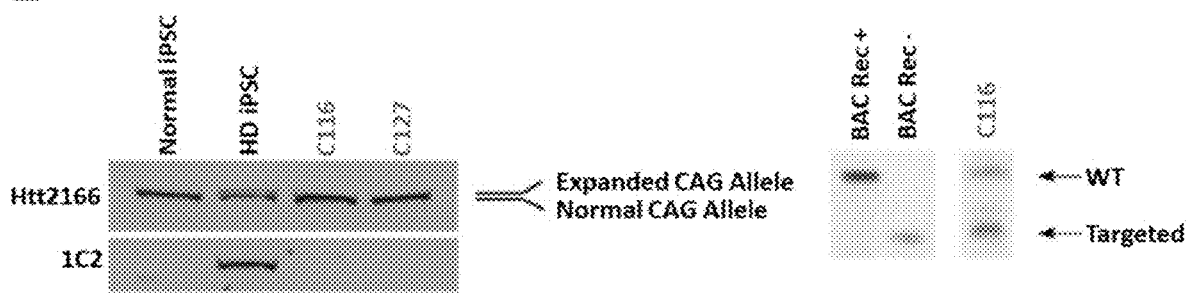
*Fig. 1, cont'd.*

F

| Cells Transfected | Clones Screened (G418r) | CAG + | Targeted |
|---|---|---|---|
| 5 x 10⁶ | 203 | 12 (6%) | 2 (1%) |

6 His- MBP- TEV- ZIKA- Flag-NLS-HA-Cas9 nickase- NLS ~200kD

B

LNA (2',4'-BNA)

BNA$^{NC}$ (2',4'-BNA$^{NC}$)

SEQUENCE LISTING

<160> NUMBER OF SEQ ID NOS: 37

<210> SEQ ID NO 1
<211> LENGTH: 43
<212> TYPE: PRT
<213> ORGANISM: Zika virus

<400> SEQUENCE: 1

Glu Asn Leu Glu Tyr Arg Ile Met Leu Ser Val His Gly Ser Gln His
1               5                   10                  15

Ser Gly Met Ile Val Asn Asp Thr Gly His Glu Thr Asp Glu Asn Arg
            20                  25                  30

Ala Lys Val Glu Ile Thr Pro Asn Ser Pro Arg
            35                  40

<210> SEQ ID NO 2
<211> LENGTH: 5
<212> TYPE: PRT

```
<213> ORGANISM: S. thermophilius

<400> SEQUENCE: 2

Asn Gly Gly Asn Gly
1               5

<210> SEQ ID NO 3
<211> LENGTH: 6
<212> TYPE: PRT
<213> ORGANISM: S. thermophilius

<400> SEQUENCE: 3

Asn Asn Ala Ala Ala Trp
1               5

<210> SEQ ID NO 4
<211> LENGTH: 6
<212> TYPE: PRT
<213> ORGANISM: S. thermophilius

<400> SEQUENCE: 4

Asn Asn Ala Gly Ala Ala
1               5

<210> SEQ ID NO 5
<211> LENGTH: 7
<212> TYPE: PRT
<213> ORGANISM: S. thermophilius

<400> SEQUENCE: 5

Asn Asn Asn Gly Ala Thr Thr
1               5

<210> SEQ ID NO 6
<211> LENGTH: 7
<212> TYPE: PRT
<213> ORGANISM: C. jejuni

<400> SEQUENCE: 6

Asn Asn Asn Asn Ala Cys Ala
1               5

<210> SEQ ID NO 7
<211> LENGTH: 8
<212> TYPE: PRT
<213> ORGANISM: N. meningitides

<400> SEQUENCE: 7

Asn Asn Asn Asn Gly Ala Thr Thr
1               5

<210> SEQ ID NO 8
<211> LENGTH: 8
<212> TYPE: PRT
<213> ORGANISM: P. multocida

<400> SEQUENCE: 8

Gly Asn Asn Asn Cys Asn Asn Ala
1               5

<210> SEQ ID NO 9
<211> LENGTH: 22
<212> TYPE: DNA
<213> ORGANISM: Artificial
<220> FEATURE:
```

```
<223> OTHER INFORMATION: CRISPR guide RNA
<220> FEATURE:
<221> NAME/KEY: misc_feature
<222> LOCATION: (1)..(3)
<223> OTHER INFORMATION: May be present or absent
<220> FEATURE:
<221> NAME/KEY: misc_feature
<222> LOCATION: (4)..(20)
<223> OTHER INFORMATION: n is a, c, g, or t

<400> SEQUENCE: 9
nnnnnnnnnn nnnnnnnnnn rg                                              22

<210> SEQ ID NO 10
<211> LENGTH: 23
<212> TYPE: DNA
<213> ORGANISM: Artificial
<220> FEATURE:
<223> OTHER INFORMATION: CRISPR guide RNA
<220> FEATURE:
<221> NAME/KEY: misc_feature
<222> LOCATION: (1)..(3)
<223> OTHER INFORMATION: May be present or absent
<220> FEATURE:
<221> NAME/KEY: misc_feature
<222> LOCATION: (4)..(21)
<223> OTHER INFORMATION: n is a, c, g, or t

<400> SEQUENCE: 10
gnnnnnnnnn nnnnnnnnnn nrg                                             23

<210> SEQ ID NO 11
<211> LENGTH: 19
<212> TYPE: RNA
<213> ORGANISM: Artificial
<220> FEATURE:
<223> OTHER INFORMATION: CRISPR guide RNA

<400> SEQUENCE: 11
aauuucuacu guguagau                                                   19

<210> SEQ ID NO 12
<211> LENGTH: 38
<212> TYPE: RNA
<213> ORGANISM: Artificial
<220> FEATURE:
<223> OTHER INFORMATION: CRISPR guide RNA

<400> SEQUENCE: 12
aauuucuacu guguagaua auuucugcug uugcagau                              38

<210> SEQ ID NO 13
<211> LENGTH: 19
<212> TYPE: RNA
<213> ORGANISM: Artificial
<220> FEATURE:
<223> OTHER INFORMATION: CRISPR guide RNA

<400> SEQUENCE: 13
aauuuccacu guguggau                                                   19

<210> SEQ ID NO 14
<211> LENGTH: 19
<212> TYPE: RNA
<213> ORGANISM: Artificial
<220> FEATURE:
<223> OTHER INFORMATION: CRISPR guide RNA

<400> SEQUENCE: 14
```
aauuccuacu guguaggu                                              19

<210> SEQ ID NO 15
<211> LENGTH: 19
<212> TYPE: RNA
<213> ORGANISM: Artificial
<220> FEATURE:
<223> OTHER INFORMATION: CRISPR guide RNA

<400> SEQUENCE: 15
aauuucuacu auuguagau                                             19

<210> SEQ ID NO 16
<211> LENGTH: 19
<212> TYPE: RNA
<213> ORGANISM: Artificial
<220> FEATURE:
<223> OTHER INFORMATION: CRISPR guide RNA

<400> SEQUENCE: 16
aauuucuacu gcuguagau                                             19

<210> SEQ ID NO 17
<211> LENGTH: 18
<212> TYPE: RNA
<213> ORGANISM: Artificial
<220> FEATURE:
<223> OTHER INFORMATION: CRISPR guide RNA

<400> SEQUENCE: 17
aauuucuacu uuguagau                                              18

<210> SEQ ID NO 18
<211> LENGTH: 17
<212> TYPE: RNA
<213> ORGANISM: Artificial
<220> FEATURE:
<223> OTHER INFORMATION: CRISPR guide RNA

<400> SEQUENCE: 18
aauuucuacu uguagau                                               17

<210> SEQ ID NO 19
<211> LENGTH: 7
<212> TYPE: PRT
<213> ORGANISM: Artificial
<220> FEATURE:
<223> OTHER INFORMATION: Nuclear localization sequence

<400> SEQUENCE: 19

Pro Lys Lys Lys Arg Lys Val
1               5

<210> SEQ ID NO 20
<211> LENGTH: 7
<212> TYPE: PRT
<213> ORGANISM: Artificial
<220> FEATURE:
<223> OTHER INFORMATION: Nuclear localization sequence

<400> SEQUENCE: 20

Pro Lys Lys Lys Arg Arg Val
1               5

<210> SEQ ID NO 21

```
<211> LENGTH: 16
<212> TYPE: PRT
<213> ORGANISM: Artificial
<220> FEATURE:
<223> OTHER INFORMATION: Nuclear localization sequence

<400> SEQUENCE: 21

Lys Arg Pro Ala Ala Thr Lys Lys Ala Gly Gln Ala Lys Lys Lys Lys
1               5                   10                  15

<210> SEQ ID NO 22
<211> LENGTH: 4
<212> TYPE: PRT
<213> ORGANISM: Artificial
<220> FEATURE:
<223> OTHER INFORMATION: Peptide linker

<400> SEQUENCE: 22

Gly Gly Gly Gly
1

<210> SEQ ID NO 23
<211> LENGTH: 5
<212> TYPE: PRT
<213> ORGANISM: Artificial
<220> FEATURE:
<223> OTHER INFORMATION: Peptide linker

<400> SEQUENCE: 23

Pro Ser Gly Ser Pro
1               5

<210> SEQ ID NO 24
<211> LENGTH: 5
<212> TYPE: PRT
<213> ORGANISM: Artificial
<220> FEATURE:
<223> OTHER INFORMATION: Peptide linker

<400> SEQUENCE: 24

Pro Ser Pro Ser Pro
1               5

<210> SEQ ID NO 25
<211> LENGTH: 4
<212> TYPE: PRT
<213> ORGANISM: Artificial
<220> FEATURE:
<223> OTHER INFORMATION: Peptide linker

<400> SEQUENCE: 25

Lys Lys Lys Lys
1

<210> SEQ ID NO 26
<211> LENGTH: 4
<212> TYPE: PRT
<213> ORGANISM: Artificial
<220> FEATURE:
<223> OTHER INFORMATION: Peptide linker

<400> SEQUENCE: 26

Arg Arg Arg Arg
1

<210> SEQ ID NO 27
<211> LENGTH: 5
```

-continued

```
<212> TYPE: PRT
<213> ORGANISM: Artificial
<220> FEATURE:
<223> OTHER INFORMATION: Peptide linker

<400> SEQUENCE: 27

Ala Ser Ala Ser Ala
1               5

<210> SEQ ID NO 28
<211> LENGTH: 6
<212> TYPE: PRT
<213> ORGANISM: Artificial
<220> FEATURE:
<223> OTHER INFORMATION: Peptide linker

<400> SEQUENCE: 28

Gly Gly Ser Gly Gly Ser
1               5

<210> SEQ ID NO 29
<211> LENGTH: 5
<212> TYPE: PRT
<213> ORGANISM: Artificial
<220> FEATURE:
<223> OTHER INFORMATION: Peptide linker

<400> SEQUENCE: 29

Gly Gly Gly Gly Ser
1               5

<210> SEQ ID NO 30
<211> LENGTH: 10
<212> TYPE: PRT
<213> ORGANISM: Artificial
<220> FEATURE:
<223> OTHER INFORMATION: Peptide linker

<400> SEQUENCE: 30

Gly Gly Gly Gly Ser Gly Gly Gly Gly Ser
1               5                   10

<210> SEQ ID NO 31
<211> LENGTH: 15
<212> TYPE: PRT
<213> ORGANISM: Artificial
<220> FEATURE:
<223> OTHER INFORMATION: Peptide linker

<400> SEQUENCE: 31

Gly Gly Gly Gly Ser Gly Gly Gly Gly Ser Gly Gly Gly Gly Ser
1               5                   10                  15

<210> SEQ ID NO 32
<211> LENGTH: 20
<212> TYPE: PRT
<213> ORGANISM: Artificial
<220> FEATURE:
<223> OTHER INFORMATION: Peptide linker

<400> SEQUENCE: 32

Gly Gly Gly Gly Ser Gly Gly Gly Gly Ser Gly Gly Gly Gly Ser Gly
1               5                   10                  15

Gly Gly Gly Ser
            20
```

```
<210> SEQ ID NO 33
<211> LENGTH: 25
<212> TYPE: PRT
<213> ORGANISM: Artificial
<220> FEATURE:
<223> OTHER INFORMATION: Peptide linker

<400> SEQUENCE: 33

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 34
<211> LENGTH: 30
<212> TYPE: PRT
<213> ORGANISM: Artificial
<220> FEATURE:
<223> OTHER INFORMATION: Peptide linker

<400> SEQUENCE: 34

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 35
<211> LENGTH: 32
<212> TYPE: PRT
<213> ORGANISM: Artificial
<220> FEATURE:
<223> OTHER INFORMATION: Peptide linker

<400> SEQUENCE: 35

Gly Gly Gly Gly Ser Gly Gly Gly Gly Ser Gly Gly Gly Gly Ser Phe
1               5                   10                  15

Lys Gly Gly Gly Gly Ser Gly Gly Gly Gly Ser Gly Gly Gly Gly Ser
            20                  25                  30

<210> SEQ ID NO 36
<211> LENGTH: 32
<212> TYPE: PRT
<213> ORGANISM: Artificial
<220> FEATURE:
<223> OTHER INFORMATION: Peptide linker

<400> SEQUENCE: 36

Gly Gly Gly Gly Ser Gly Gly Gly Gly Ser Gly Gly Gly Gly Ser Val
1               5                   10                  15

Ala Gly Gly Gly Gly Ser Gly Gly Gly Gly Ser Gly Gly Gly Gly Ser
            20                  25                  30

<210> SEQ ID NO 37
<211> LENGTH: 129
<212> TYPE: DNA
<213> ORGANISM: Artificial
<220> FEATURE:
<223> OTHER INFORMATION: DNA encoding cell penetrating peptide

<400> SEQUENCE: 37
gagaatctgg aataccgtat catgttaagc gtgcatggat cacagcattc aggaatgatt      60
gtgaacgaca caggacatga aactgatgaa aaccgcgcga agtggaaat cactcccaac      120 agtccccgt                                                            129
```

ZIKA AS A CELL PENETRATING PEPTIDE FOR DELIVERY TO THE BRAIN

CROSS-REFERENCE TO RELATED APPLICATIONS

This application claims priority to and benefit of U.S. Ser. No. 62/670,609, filed on May 11, 2018, which is incorporated herein by reference in its entirety for all purposes.

INCORPORATION BY REFERENCE OF SEQUENCE LISTING PROVIDED AS A TEXT FILE

A Sequence Listing is provided herewith as a text file, "BUCK-P063US_ST25.txt" created on Dec. 3, 2020, and having a size of 7.87 KB. The contents of the text file are incorporated by reference herein in their entirety.

BACKGROUND

Considerable attention has been devoted to developing reagents and methods for delivering bioactive agents to particular tissues, cells, and/or subcellular locations. For example, delivery of large molecules, such as an antisense, or RNAi molecules, or proteins, is difficult as such compounds are generally not able to penetrate cell membranes. Moreover, when they are often modified to be able to penetrate cell membranes, they often lack of selectivity for the tissue of interest and therefore increase the risk of off-target activity and consequently present serious safety concerns.

Several different delivery methods have been tried with varying amounts of success, from viral to nanoparticle delivery (1-3). These methods can be invasive (direct injection into organ), elicit an immune response or have inflexible dosing regimens.

In the context of gene therapy, most gene editing agents have often been delivered via plasmid DNA encapsulated in viral-derived vectors such as lentivirus (LV) vectors, adeno virus (AV) vectors, and adeno-associated virus (AAV) vectors. Unfortunately, this type of approach has been plagued with serious issues for the patients including, inter alia: i) increased risk of insertional mutagenesis; ii) increased risks of hepatotoxicity upon interaction of viral vector with Kupffer cells; and iii) only transient pharmacological benefit for the patient triggered by immunogenic response against the treated cells. Attempts to find more effective and safer ways to deliver gene editing agents thus far have been elusive.

An underutilized approach involves delivering the CRISPR/Cas9 as a fully purified protein, conjugated to its target gRNAs as a ribonucleoprotein (RNP) (4, 5). Gene modifying proteins have been delivered to cells and mice by attaching a cell penetrating peptide (CPPs) to the protein (6-9). This method has several advantages: dosage can be controlled and is transient, doses can be given repeatedly and they can be administered peripherally. The number of cell penetrating peptides used to deliver proteins is fairly limited in vivo, particularly with respect to the brain.

SUMMARY

We have successfully designed a cell penetrating peptide (CPP) that crosses the blood brain barrier and delivers Cas9 (or other "effectors") into target cells (see, e.g., Example 1). Many of the current cell penetrating peptides are derived from viral proteins. Using the current viral genome database and the accompanying structural data on these viruses we have design new CPPs (e.g., a CPP derived from Zika virus) that targets neural and other tissues.

The CPPs described herein have the potential to deliver other types of therapeutics including, but not limited to, antisense oligonucleotides, siRNAs, purified proteins, coating virus particles or nanoparticles.

Accordingly, various embodiments contemplated herein may include, but need not be limited to, one or more of the following:

EMBODIMENT 1

A construct comprising a cell penetrating peptide attached to an effector that is to be delivered into a cell, wherein:
said cell penetrating peptide comprises a Zika cell penetrating peptide (Zika CPP); and
said effector is selected from the group consisting of a protein, a nucleic acid, an organic compound, a viral particle, and a nanoparticle.

EMBODIMENT 2

The construct of embodiment 1, wherein said construct is effective to transfer a functional effector into a neural cell.

EMBODIMENT 3

The construct according to any one of embodiments 1-2, wherein said construct is effective to transfer a functional effector into a cell that is not a neural cell.

EMBODIMENT 4

The construct according to any one of embodiments 1-3, wherein said cell penetrating peptide comprises a cell penetrating peptide derived from Zika virus.

EMBODIMENT 5

The construct of embodiment 4, wherein the amino acid sequence of said cell penetrating peptide comprises the sequence ENLEYRIMLSVHGSQHSGMIVNDTG HETDENRAKVEITPNSPR (SEQ ID NO:1), or a fragment thereof that retains the ability to penetrate into a target cell.

EMBODIMENT 6

The construct of embodiment 5, wherein the amino acid sequence of said cell penetrating peptide comprises the sequence ENLEYRIMLSVHGSQHSGMIVNDTG HETDENRAKVEITPNSPR (SEQ ID NO:1), or a fragment thereof that retains the ability to penetrate into a mammalian cell.

EMBODIMENT 7

The construct of embodiment 5, wherein the amino acid sequence of said cell penetrating peptide comprises the sequence ENLEYRIMLSVHGSQHSGMIVNDTG HETDENRAKVEITPNSPR (SEQ ID NO:1), or a fragment thereof that retains the ability to penetrate into a non-mammalian eukaryotic cell.

EMBODIMENT 8

The construct of embodiment 4, wherein the amino acid sequence of said cell penetrating peptide has at least 70%, or at least 785%, or at least 80%, or at least 85%, or at least 90%, or at least 95%, or at least 98% sequence identity with the amino acid sequence ENLEYRIMLSVHGSQHSG-MIVNDTG HETDENR AKVEIT PNSPR (SEQ ID NO:1) and retains the ability to penetrate into mammalian cells.

EMBODIMENT 9

The construct of embodiment 4, wherein the amino acid sequence of said cell penetrating peptide consists of the sequence ENLEYRIMLSVHGSQHSGMIVNDTG HETDENR AKVEIT PNSPR (SEQ ID NO:1).

EMBODIMENT 10

The construct according to any one of embodiments 1-9, wherein said cell penetrating peptide ranges in length up to 100 amino acids, or up to 90 amino acids, or up to 80 amino acids, or up to 70 amino acids, or up to 60 amino acids, or up to 50 amino acids, or up to 49 amino acids, or up to 48 amino acids, or up to 47 amino acids, or up to 46 amino acids, or up to 45 amino acids, or up to 44 amino acids, or up to 43 amino acids.

EMBODIMENT 11

The construct according to any one of embodiments 1-10, wherein said cell penetrating peptide is attached to said effector by a non-covalent interaction.

EMBODIMENT 12

The construct of embodiment 11, wherein said non-covalent interaction comprises a biotin/avidin interaction.

EMBODIMENT 13

The construct according to any one of embodiments 1-10, wherein said cell penetrating peptide is chemically conjugated to said effector.

EMBODIMENT 14

The construct of embodiment 13, wherein said cell penetrating peptide is chemically conjugated to said effector via a non-cleavable linker.

EMBODIMENT 15

The construct of embodiment 13, wherein said cell penetrating peptide is chemically conjugated to said effector via a cleavable linker.

EMBODIMENT 16

The construct of embodiment 13, wherein said cell penetrating peptide is chemically conjugated to said effector via a cleavable linker comprising a disulfide linker or an acid-labile linker.

EMBODIMENT 17

The construct of embodiment 13, wherein said cell penetrating peptide is chemically conjugated to said effector via an acid label linker comprising a moiety selected from the group consisting of a hydrazone, an acetal, a cis-aconitate-like amide, a silyl ether.

EMBODIMENT 18

The construct of embodiment 13, wherein said cell penetrating peptide is chemically conjugated to said effector via a non-amino acid, non-peptide linker shown in Table 2.

EMBODIMENT 19

The construct according to any one of embodiments 1-10, wherein said effector comprises a polypeptide and said construct comprise a fusion protein.

EMBODIMENT 20

The construct of embodiment 19, wherein said fusion protein comprises said cell penetrating peptide directly attached to said effector.

EMBODIMENT 21

The construct of embodiment 19, wherein said fusion protein comprises said cell penetrating peptide attached to said effector by an amino acid.

EMBODIMENT 22

The construct of embodiment 19, wherein said fusion protein comprises said cell penetrating peptide attached to said effector by a peptide linker.

EMBODIMENT 23

The construct of embodiment 22, wherein said linker comprises an amino acid sequence cleavable by a protease.

EMBODIMENT 24

The construct of embodiment 23, wherein said linker comprises an amino acid sequence cleavable by a cathepsin.

EMBODIMENT 25

The construct according to any one of embodiments 22-24, wherein said peptide linker comprises a dipeptide valine-citrulline (Val-Cit), or Phe-Lys.

EMBODIMENT 26

The construct of embodiment 19, wherein said fusion protein comprises said cell penetrating peptide attached to said effector by an amino acid or peptide linker shown in Table 2.

EMBODIMENT 27

The construct according to any one of embodiments 1-26, wherein said effector comprises a protein.

EMBODIMENT 28

The construct of embodiment 27, wherein said effector comprises a targeted endonuclease.

EMBODIMENT 29

The construct of embodiment 28, wherein said targeted endonuclease comprise a class 2 CRISPR/Cas endonuclease.

EMBODIMENT 30

The construct of embodiment 29, wherein said class 2 CRISPR/Cas endonuclease is a type II CRISPR/Cas endonuclease.

EMBODIMENT 31

The construct of embodiment 30, wherein the class 2 CRISPR/Cas endonuclease comprises a Cas9 protein.

EMBODIMENT 32

The construct of embodiment 31, wherein said Cas9 protein is selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

EMBODIMENT 33

The construct of embodiment 32, wherein said Cas9 protein comprises a *Streptococcus pyogenes* Cas9 protein (spCas9).

EMBODIMENT 34

The construct of embodiment 32, wherein said Cas9 protein comprises a *Staphylococcus aureus* Cas9 protein (saCas9).

EMBODIMENT 35

The construct of embodiment 32, wherein said Cas9 protein comprises a *Streptococcus thermophilus* Cas9 protein.

EMBODIMENT 36

The construct of embodiment 32, wherein said Cas9 protein comprises a *Neisseria meningitides* Cas9 protein (nmCas9).

EMBODIMENT 37

The construct of embodiment 32, wherein said Cas9 protein comprises a *Treponema denticola* Cas9 protein (tdCas9).

EMBODIMENT 38

The construct of embodiment 31, wherein said Cas9 protein is a Cas9 protein fused to a repressor or an activator domain.

EMBODIMENT 39

The construct of embodiment 38, wherein said Cas9 protein is fused to an activator domain.

EMBODIMENT 40

The construct of embodiment 39, wherein said Cas9 protein is fused to a VP64 transcriptional activator.

EMBODIMENT 41

The construct of embodiment 39, wherein said Cas9 protein is fused to a VP16 transcriptional activator.

EMBODIMENT 42

The construct of embodiment 38, wherein said Cas9 protein is fused to a repressor domain.

EMBODIMENT 43

The construct of embodiment 42, wherein said Cas9 is fused to a Kruppel associated box (KRAB) domain.

EMBODIMENT 44

The construct of embodiment 29, wherein said class 2 CRISPR/Cas endonuclease is a type V or type VI CRISPR/Cas endonuclease.

EMBODIMENT 45

The construct of embodiment 44, wherein the class 2 CRISPR/Cas protein is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

EMBODIMENT 46

The construct of embodiment 45, wherein the class 2 CRISPR/Cas protein comprises a Cpf1 protein.

EMBODIMENT 47

The construct according to any one of embodiments 28-46, wherein said effector is complexed with a guide RNA to form a ribonucleoprotein complex.

EMBODIMENT 48

The construct of embodiment 47, wherein said guide RNA comprises one or more bridged nucleic acids.

EMBODIMENT 49

The construct of embodiment 48, wherein said bridged nucleic acid comprises one or more N-methyl substituted BNAs (2',4'-BNA$^{NC}$[N-Me]).

EMBODIMENT 50

The construct of embodiment 47, wherein said guide RNA comprises one or more locked nucleic acids (LNAs).

EMBODIMENT 51

The method according to any one of embodiments 47-50, wherein said guide RNA (gRNA) targets a gene selected from the group consisting of HTT (e.g., for Huntington's disease), AADC, TH, GCH-1 (e.g., for Parkinson's disease), SOD1 (e.g., for ALS), PGC-la (e.g. for Alzheimer's disease), UBE3A (e.g., for Angelman Syndrome), NECO2 (e.g., for Retts), and SNRPN (e.g., for Prader-Willi).

EMBODIMENT 52

The construct of embodiment 28, wherein said targeted endonuclease comprises a zinc finger protein.

EMBODIMENT 53

The construct of embodiment 28, wherein said targeted endonuclease comprises a TALEN.

EMBODIMENT 54

The construct according to any one of embodiments 1-18, wherein said effector comprises a viral particle.

EMBODIMENT 55

The construct of embodiment 54, wherein said cell penetrating peptide is chemically conjugated to said viral particle.

EMBODIMENT 56

The construct of embodiment 54, wherein said cell penetrating peptide is expressed as a component of the viral particle coating.

EMBODIMENT 57

The construct according to any one of embodiments 55-56, wherein said viral particle is selected from the group consisting of an adenovirus, an adeno-associated virus, and a lentivirus.

EMBODIMENT 58

The construct according to any one of embodiments 1-18, wherein said effector comprises a nucleic acid.

EMBODIMENT 59

The construct of embodiment 58, wherein said effector comprise a nucleic acid selected from the group consisting of a DNA, an RNA, an siRNA, an antisense oligonucleotide, a transposon, and a guide RNA (gRNA).

EMBODIMENT 60

The construct of embodiment 62, wherein said effector comprises a guide RNA (gRNA).

EMBODIMENT 61

A method of delivering an effector into a cell, said method comprising contacting said cell with a construct according to any one of embodiments 1-60.

EMBODIMENT 62

The method of embodiment 61, wherein said construct is contacted to said cell ex vivo.

EMBODIMENT 63

The method of embodiment 62, wherein said cell comprises a cell from a cell line.

EMBODIMENT 64

The method of embodiment 63, wherein said cell comprises a neuronal cell.

EMBODIMENT 65

The method of embodiment 62, wherein said cell comprises a stem cell.

EMBODIMENT 66

The method of embodiment 65, wherein said cell comprise a stem cell selected from the group consisting of an adult stem cell, an embryonic stem cell, a cord blood stem cell, a peripheral blood stem cell (PBSC), and an induced pluripotent stem cell.

EMBODIMENT 67

The method of embodiment 61, wherein said construct is contacted to said cell in vivo.

EMBODIMENT 68

The method of embodiment 67, wherein said contacting comprises administering said construct to a mammal.

EMBODIMENT 69

The method of embodiment 68, wherein said mammal is a human.

EMBODIMENT 70

The method of embodiment 68, wherein said mammal is a non-human mammal.

EMBODIMENT 71

The method according to any one of embodiments 61-70, wherein said effector comprises a targeted endonuclease.

EMBODIMENT 72

The method of embodiment 71, wherein said construct comprises a construct according to any one of embodiments 28-37, and 44-46.

EMBODIMENT 73

The method according to any one of embodiments 71-72, wherein a guide RNA is delivered to said cell and said guide RNA is a component of a ribonucleoprotein complex with said targeted endonuclease comprising said construct.

EMBODIMENT 74

The method according to any one of embodiments 71-72, wherein a guide RNA is delivered to said cell in a separate construct from the construct comprising a CPP attached to an effector.

EMBODIMENT 75

The method of embodiment 74, wherein said guide RNA is delivered using a viral vector.

EMBODIMENT 76

The method of embodiment 75, wherein said viral vector comprises a vector selected from an adenoviral vector, an adenovirus associated vector, and a lentiviral vector.

Definitions

The terms "protein" and "polypeptide" are used interchangeably to refer to a series of amino acid residues joined by peptide bonds (i.e., a polymer of amino acids) and include modified amino acids (e.g., phosphorylated, glycated, glycosolated, etc.) and amino acid analogs. Illustrative polypeptides or proteins include gene products, naturally occurring proteins, homologs, paralogs, fragments and other equivalents, variants, and analogs of the above.

An "effector" refers to a moiety/molecule that is to be delivered into a target cell. The effector typically has a characteristic activity that is desired to be delivered to the target. Effector molecules include, but are not limited to proteins (e.g., enzymes, antibodies, etc.), a nucleic acid (e.g., DNA, RNA, ssDNA, antisense oligonucleotides, etc.), an organic compound, a nanoparticle, as a coating of viral capsids, and the like. In certain embodiments an effector comprises a targeted endonuclease, e.g., as described herein.

A "functional effector" refers to an effector that retains its function after delivery into a cell. Thus, for example, a functional targeted endonuclease is an endonuclease that retains its endonuclease activity and targeting ability (e.g., in combination with a suitable guide RNA) after entry into a cell.

The terms "subject," "individual," "mammal", and "patient" may be used interchangeably and refer to humans, as well as non-human mammals (e.g., non-human primates, canines, equines, felines, porcines, bovines, ungulates, lagomorphs, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

A "host cell," as used herein, denotes an in vivo or in vitro eukaryotic cell, or a cell from a multicellular organism (e.g., a cell line) cultured as a unicellular entity, which eukaryotic cells can be, or have been, used as recipients for a nucleic acid (e.g., a donor template nucleic acid), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a eukaryotic host cell is a genetically modified eukaryotic host cell, by virtue of introduction into a suitable eukaryotic host cell of a heterologous nucleic acid, e.g., an exogenous nucleic acid that is foreign to the eukaryotic host cell, or a recombinant nucleic acid that is not normally found in the eukaryotic host cell.

The term "stem cell" is used herein to refer to a cell (e.g., plant stem cell, vertebrate stem cell) that has the ability both to self-renew and to generate a differentiated cell type (see Morrison et al. (1997) Cell 88:287-298). In the context of cell ontogeny, the adjective "differentiated", or "differentiating" is a relative term. A "differentiated cell" is a cell that has progressed further down the developmental pathway than the cell it is being compared with. Thus, pluripotent stem cells (described below) can differentiate into lineage-restricted progenitor cells (e.g., mesodermal stem cells), which in turn can differentiate into cells that are further restricted (e.g., neuron progenitors), which can differentiate into end-stage cells (i.e., terminally differentiated cells, e.g., neurons, cardiomyocytes, etc.), which play a characteristic role in a certain tissue type, and may or may not retain the capacity to proliferate further. Stem cells may be characterized by both the presence of specific markers (e.g., proteins, RNAs, etc.) and the absence of specific markers. Stem cells may also be identified by functional assays both in vitro and in vivo, particularly assays relating to the ability of stem cells to give rise to multiple differentiated progeny.

Stem cells of interest include, but are not limited to pluripotent stem cells (PSCs). The term "pluripotent stem cell" or "PSC" is used herein to mean a stem cell capable of producing all cell types of the organism. Therefore, a PSC can give rise to cells of all germ layers of the organism (e.g., the endoderm, mesoderm, and ectoderm of a vertebrate). Pluripotent cells are capable of forming teratomas and of contributing to ectoderm, mesoderm, or endoderm tissues in a living organism. Pluripotent stem cells of plants are capable of giving rise to all cell types of the plant (e.g., cells of the root, stem, leaves, etc.).

Stem cells of animals can be derived in a number of different ways. For example, embryonic stem cells (ESCs) are derived from the inner cell mass of an embryo (Thomson et. Al. (1998) *Science,* 282(5391): 1145-1147) whereas induced pluripotent stem cells (iPSCs) are derived from somatic cells (Takahashi et. Al. (2007) *Cell,* 131(5): 861-872; Takahashi et. Al. (2007) *Nat. Protoc.* 2(12): 3081-3079; Yu et. Al. (2007) *Science,* 318(5858): 1917-1920). Because the term PSC refers to pluripotent stem cells regardless of their derivation, the term PSC encompasses the terms ESC and iPSC, as well as the term embryonic germ stem cells (EGSC), which are another example of a PSC. PSCs may be in the form of an established cell line, they may be obtained directly from primary embryonic tissue, or they may be derived from a somatic cell. PSCs can be target cells of the methods described herein. In certain embodiments the methods described herein expressly exclude the use of embryonic stem cells or cells derived therefrom.

By "induced pluripotent stem cell" or "iPSC" it is meant a PSC that is derived from a cell that is not a PSC (i.e., from a cell this is differentiated relative to a PSC). iPSCs can be derived from multiple different cell types, including terminally differentiated cells. iPSCs have an ES cell-like morphology, growing as flat colonies with large nucleo-cytoplasmic ratios, defined borders and prominent nuclei. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT, and zfp42. Examples of methods of generating and characterizing iPSCs may be found in, for example, U.S. Patent Publication Nos. US20090047263, US20090068742, US20090191159, US20090227032, US20090246875, and US20090304646. Generally, to generate iPSCs, somatic cells are provided with reprogramming factors (e.g., Oct4, SOX2, KLF4, MYC, Nanog, Lin28, etc.) known in the art to reprogram the somatic cells to become pluripotent stem cells.

Hematopoietic stem cell transplantation (HSCT) is the transplantation of multipotent hematopoietic stem cells, usually derived from bone marrow, peripheral blood, or umbilical cord blood. In the methods described herein, the HSCT is typically autologous (the patient's own stem cells are used).

Peripheral blood stem cells (PBSCs) refers to hematopoietic stem and progenitor cells obtained from peripheral blood. Such cells are typically collected by apheresis or leukapheresis. The administered hematopoietic stem cells modified as described herein can be administered back into the subject where they then migrate to the recipient's bone marrow, a process known as stem cell homing. In In certain embodiments the PBSCs are "mobilized" by administration of G-CSF prior to collection of the cells.

The term "sequence identity" refers to a measure of similarity between two amino acid or nucleotide sequences. Sequence identity is frequently measured in terms of percentage identity (or similarity or homology); the higher the percentage, the more similar the two sequences are. Homologs or variants of the amino acid or nucleotide sequence will possess a relatively high degree of sequence identity when aligned using standard methods. In certain embodiments the recited sequence identity is over a region of at least 20, 25, 30, 35, 40, or more amino acids, or over the full-length of the referenced sequence.

Methods of alignment of sequences for comparison are well known in the art. Various programs and alignment algorithms are described in, e.g., Smith & Waterman (1981) *Adv. Appl. Math.* 2: 482; Needleman & Wunsch (197) *J. Mol. Biol.* 48: 443; Pearson & Lipman (1988) *Proc. Natl. Acad. Sci. USA*, 85: 2444; Higgins & Sharp (1988) *Gene*, 73: 237; Higgins & Sharp (1989) *CABIOS*, 5: 151; Corpet et al. (1988) *Nucleic Acids Res.* 16: 10881; and Altschul et al. (1994) *Nature Genet.* 6: 119, present a detailed consideration of sequence alignment methods and homology calculations.

The NCBI Basic Local Alignment Search Tool (BLAST) (Altschul et al. (1990) *J. Mol. Biol.* 215: 403) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

BRIEF DESCRIPTION OF THE DRAWINGS

FIG. 3, panel B) Coomassie and western blot of PZ and after purification and sterile filtration (Cas9 Cell Signaling 1:1000).

DETAILED DESCRIPTION

Figure 1:
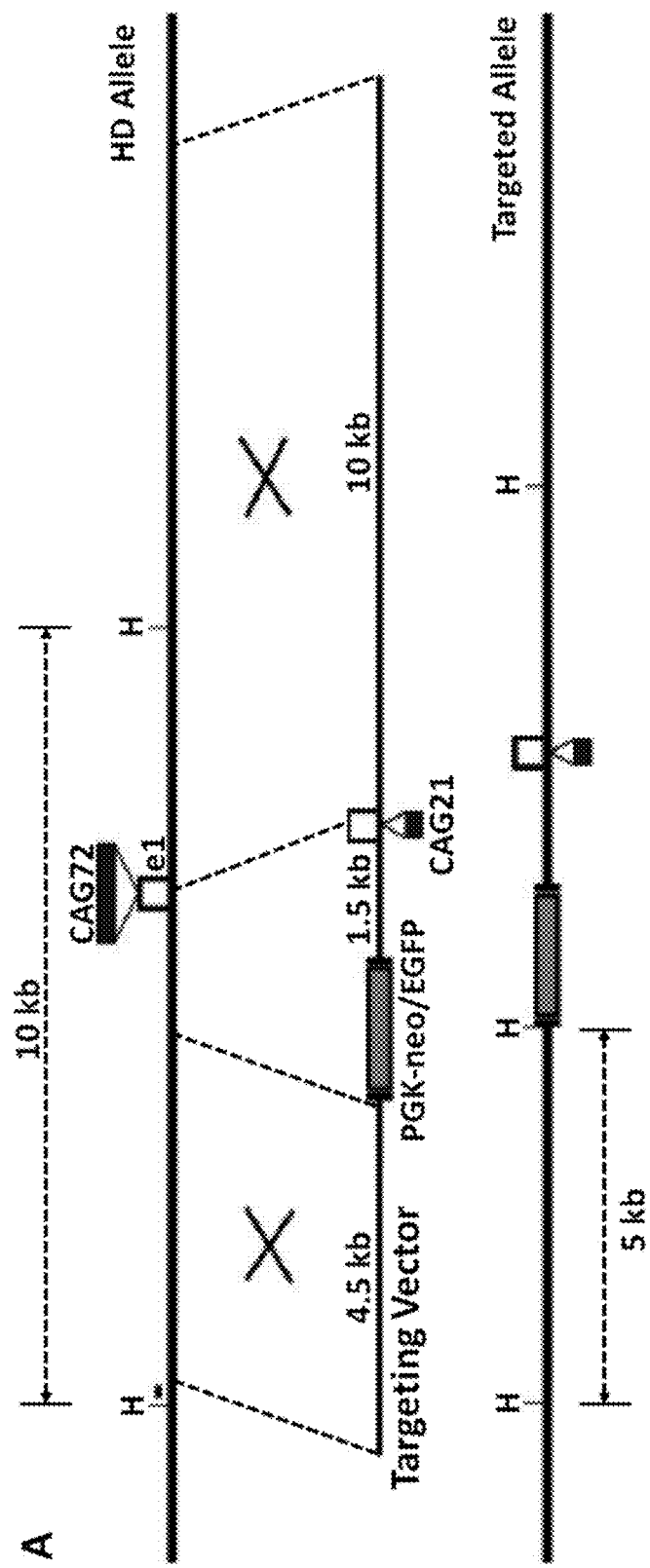
FIG. 1. Panel A) Targeting vector used for HR. Panel B) Monitoring transfection efficiency in HD-iPSCs. Panel C) PCR screen for potential targeting clones. Panel D) Southern blot analysis of clones. Panel E) Western blot demonstrating loss of polQ-expanded protein. Panel F) Summary of clones screened.
Figure 2:
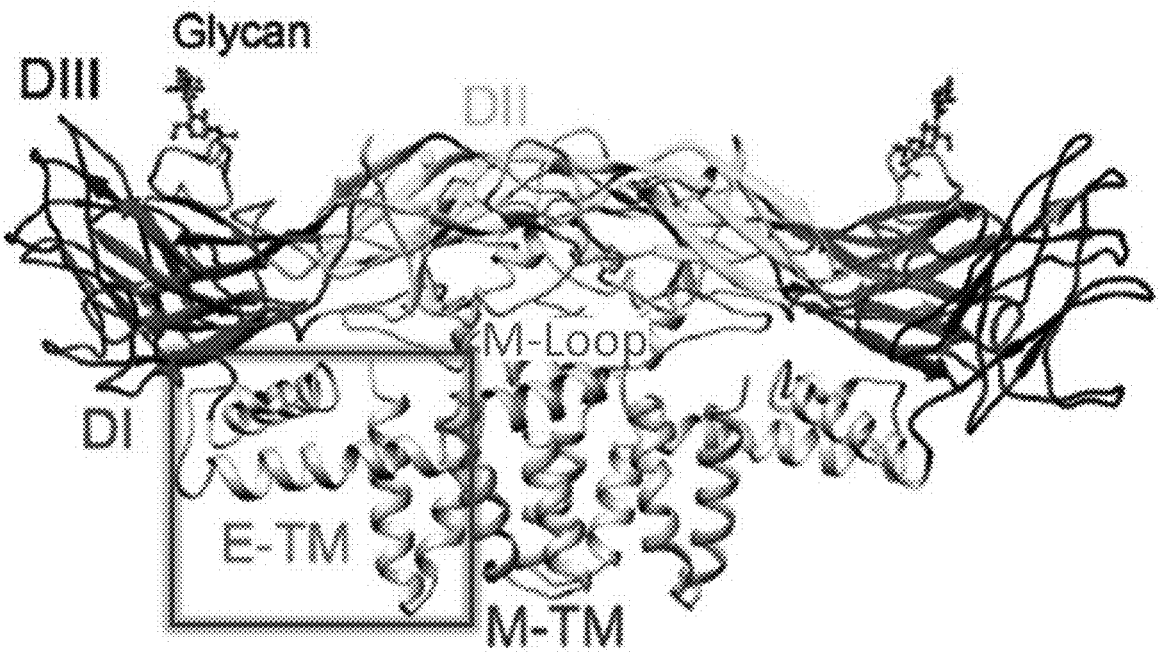
FIG. 2. Adapted from Sirohi et al. (2016) Science DOI: 10.1126/science.aaf5316) structure of Zika virus and the boxed area is the envelope protein of which a section was used as a cell penetrating peptide for our PZ protein.
Figure 3:
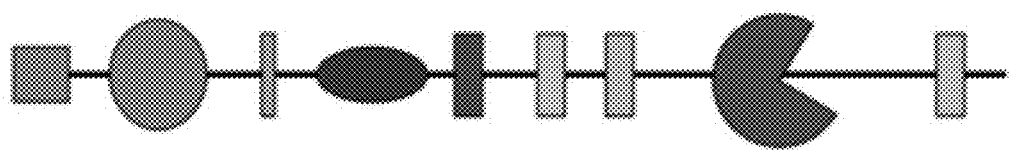
FIG. 3, panel A, shows a diagram of PZ protein with affinity tags, His and MBP, TEV cut site, ZIKA derived CPP, Flag tag, nuclear localization signal (NLS), HA tag, Cas9 nickase, NLS.
Figure 3:
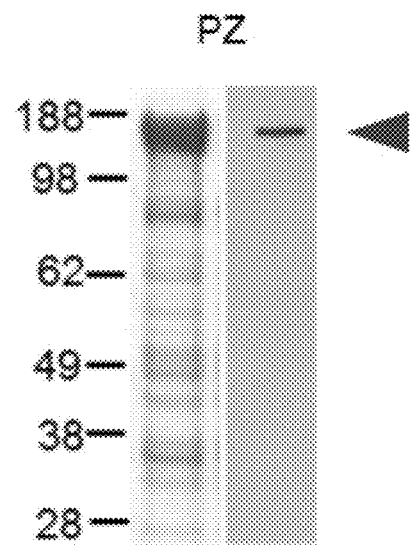
Figure 4:
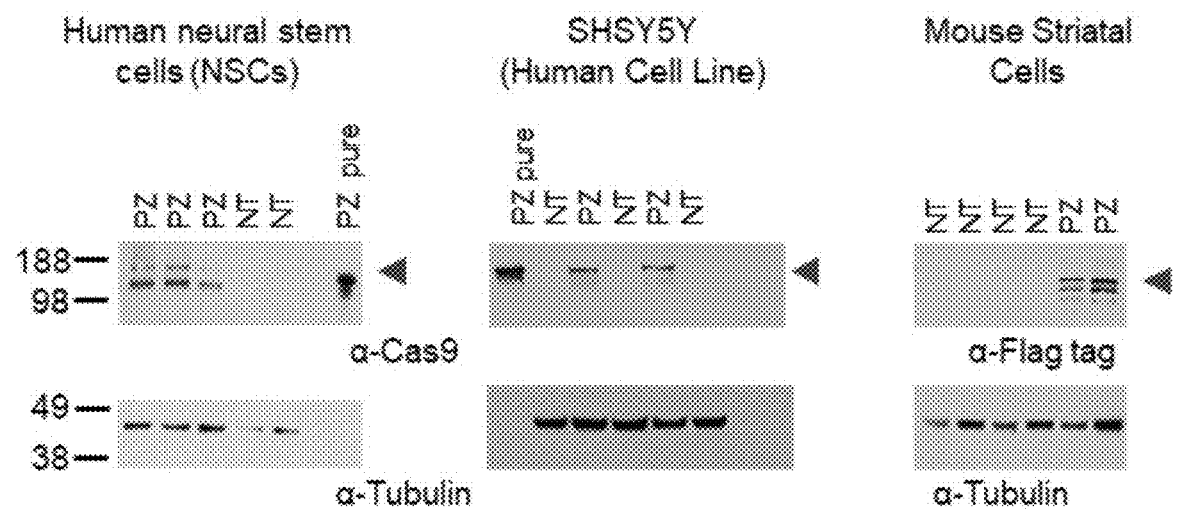
FIG. 4 illustrates western blots showing that PZ enters human neuronal stem cells, human cell line SHSYSY and mouse striatal cells. "PZ" are cells treated with 10 µg of PZ protein, "NT" are no treatment cells that did not receive the PZ protein, "PZ pure" is 50 ng of purified PZ protein.
Figure 5:
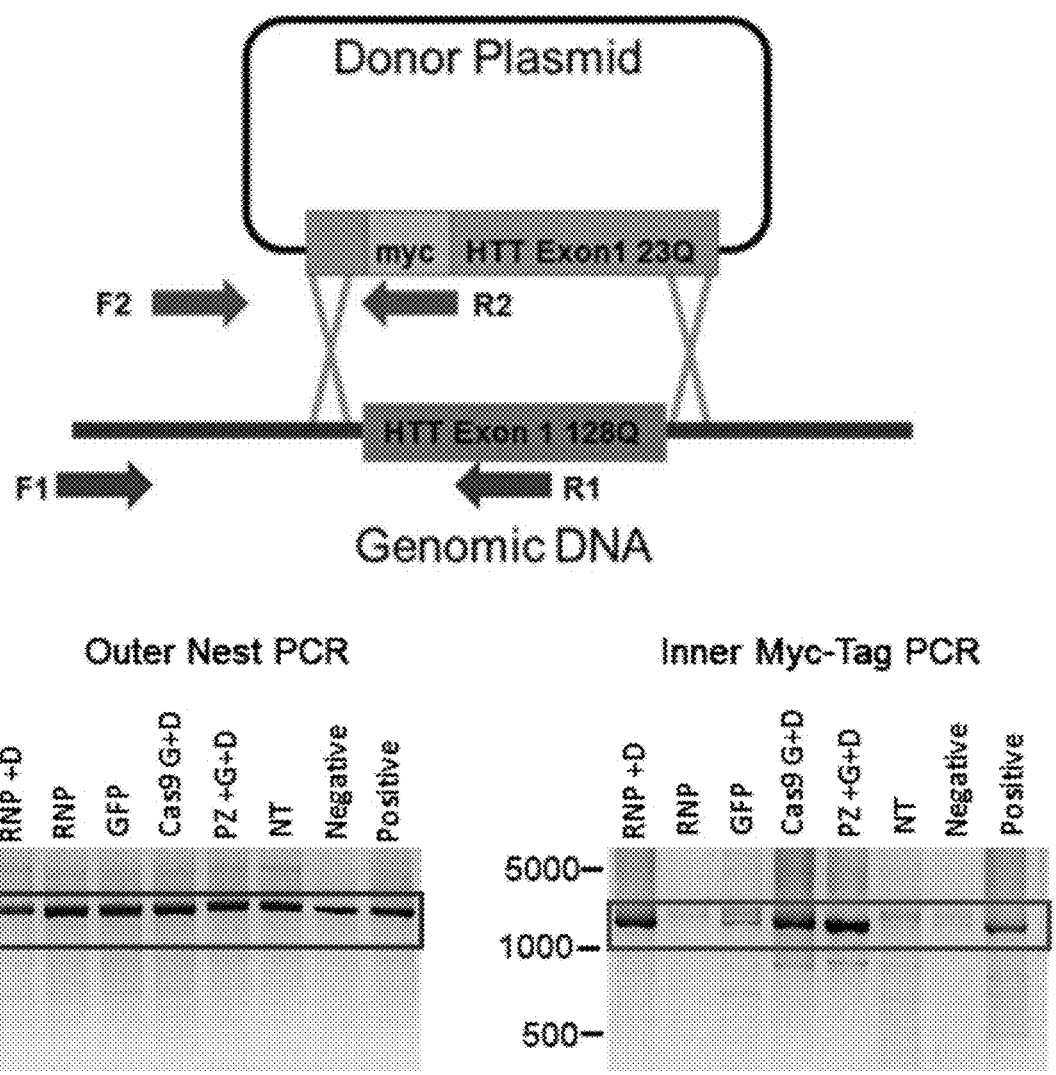
FIG. 5 shows an example of PCR detection of myc HTT Exon1 23Q recombination, in PZ treated NSCs. The region of interest is initially amplified with genomic primers, then PCR purified and myc specific PCR is done to detect insertion of the corrected HTT Exon 1 23Q donor. RNP+D is the PZ conjugate to the gRNAs on NSCs with transfected donor plasmid, RNP is PZ conjugated to gRNAs, GFP, Cas9 G+D is plasmid transfection of Cas9n, gRNAs, donor, PZ G+D is PZ protein and plasmid transfected gRNAs and donor, NT is no treatment, negative and positive are controls.
Figure 6:
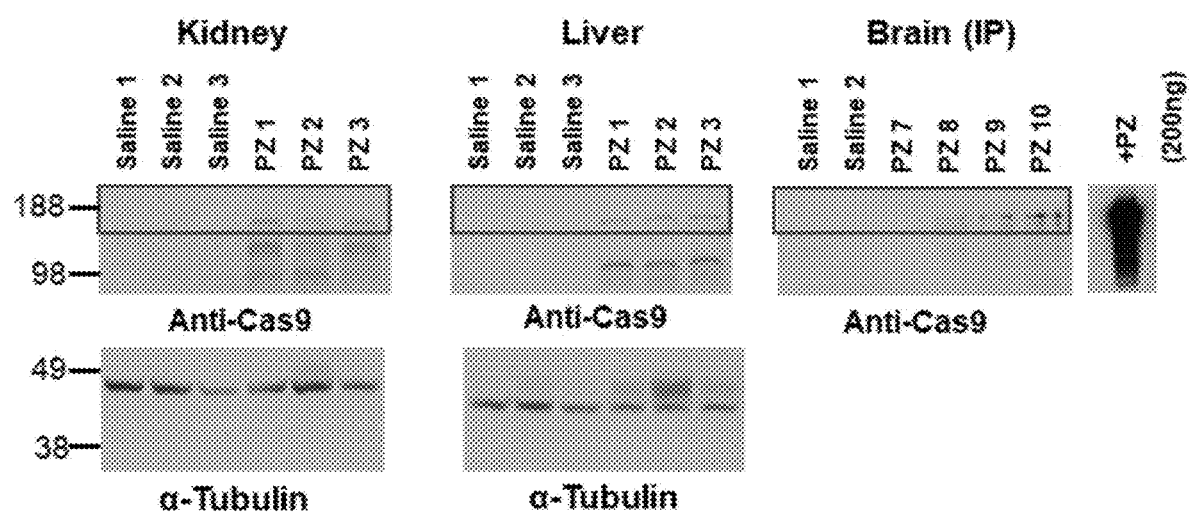
FIG. 6 illustrates detection of PZ in the kidney, liver and brain. Brain detection was done by IP pulldown using Ni/NTA beads for the His tag on the PZ protein.
Figure 7:
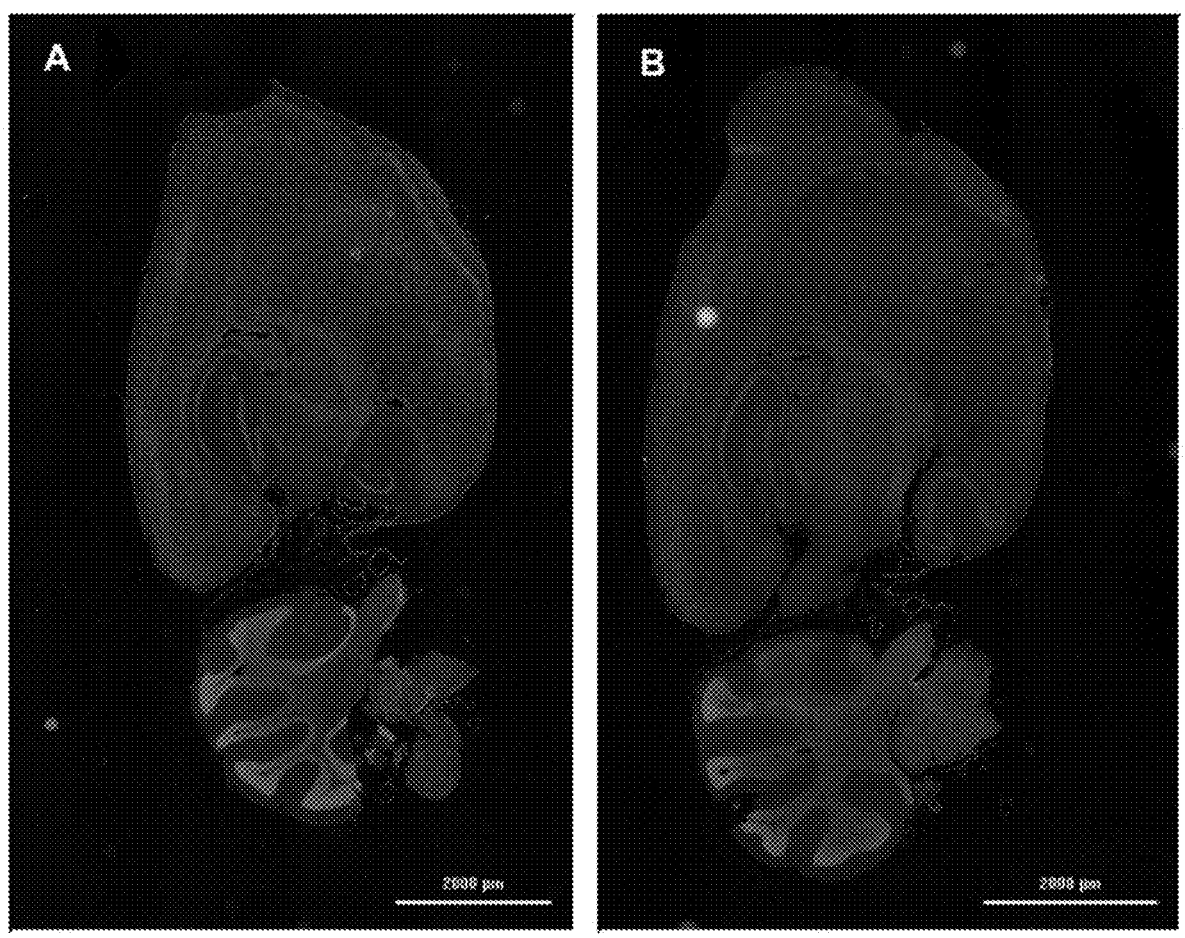
FIG. 7, panels A and B, show sagittal sections of HD YAC128 mice stained for the Flag-tag which is present on PZ protein. Panel A) mouse IV injected with a buffer solution. Panel B) Mouse injected with 300 µg of PZ.
Figure 8:
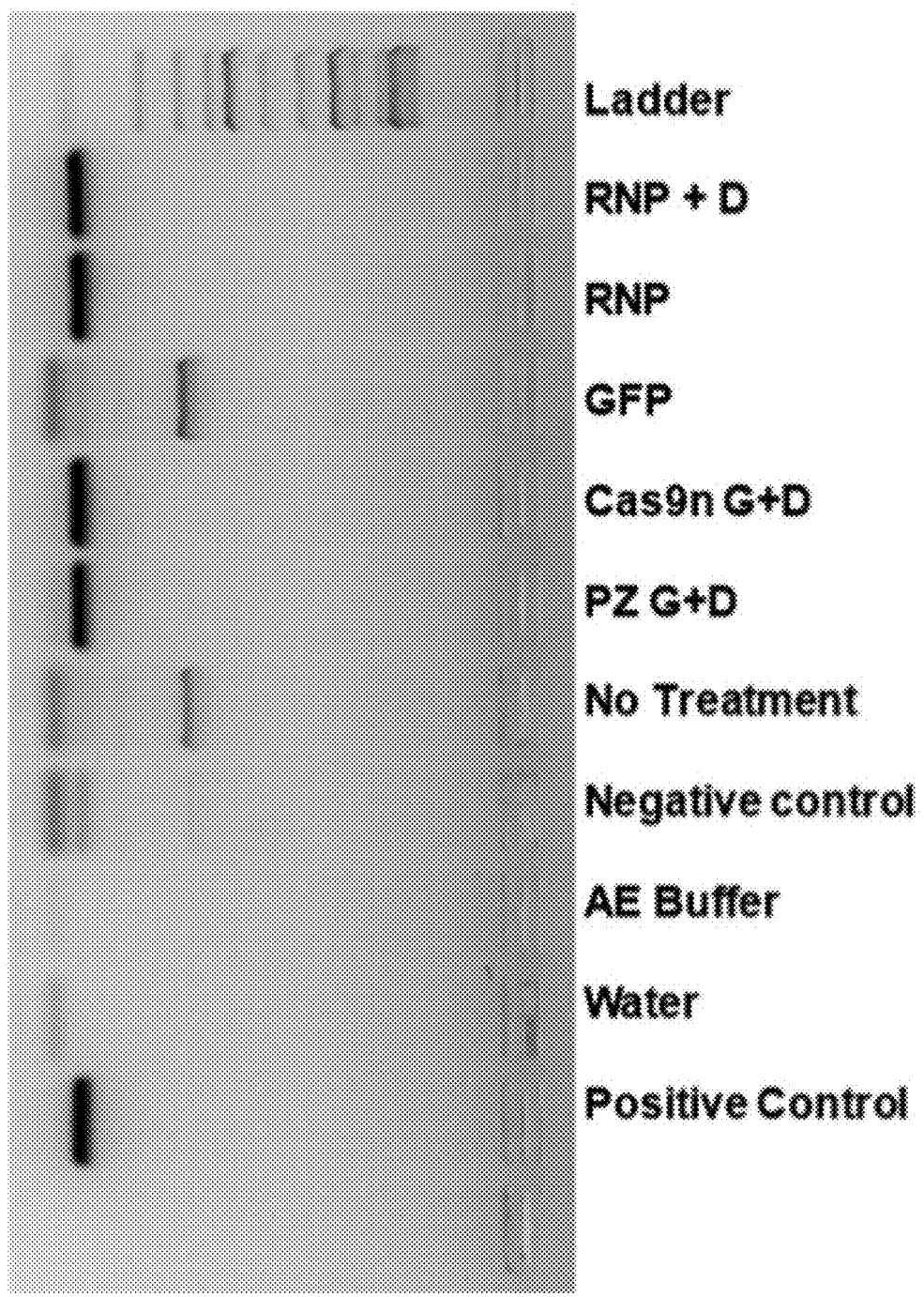
FIG. 8 illustrates an example of gRNA detection in treated NSCs. The RNA is purified and then specific primers are used to detect the gRNA presence in NSCs. RNP+D is the PZ conjugate to the gRNAs on NSCs with transfected donor plasmid, RNP is PZ conjugated to gRNAs, GFP, Cas9 G+D is plasmid transfection of Cas9n, gRNAs, donor, PZ G+D is PZ protein and plasmid transfected gRNAs and donor, NT is no treatment, negative and positive are controls.

The CRISPR/Cas9 system has the potential to transform the medical field, but still faces some significant hurdles, one of which is the delivery of the CRISPR/Cas9 system to the desired organ or tissue type. We have developed a protein-based technology to deliver this genome editing machinery (or other effectors) into disease relevant cells and tissues.

In particular we have identified novel cell penetrating peptides (e.g., a CPP derived from Zika virus) that are effective to deliver an attached "effector" into a target cell. The CPPs can be attached to an effector (e.g., a protein (e.g., an enzyme), a nucleic acid (e.g., DNA, RNA, ssDNA, antisense oligonucleotides, etc.), an organic compound, a nanoparticle, and the like) and used to "target" and deliver that effector into a particular cell in vitro and/or into a particular cell or organ in vivo. In certain embodiments the CPP is expressed (displayed) on the coating of a virus particle (e.g., adenovirus (AV), adeno-associated virus (AAV), lentivirus (LV), and the like) and can be used to deliver that subject virus into a target cell. In various embodiments the "effector" can include, but is not limited to, essentially any protein that is to be delivered into a cell. In certain embodiments the attached "effector" comprises a targeted endonuclease (e.g., an RNA guided endonuclease). Such targeted endonucleases include, but are not limited to CRISPR/Cas endonucleases, a Transcription Activator-Like Effector Nuclease (TALEN), zinc finger endonucleases, and the like.

The use of CPPs for delivery of targeted endonucleases represents a significant step forward in gene editing technology for humans and other mammals, since it helps solve many of the current delivery issues. The use of CPPs allows for less invasive treatments, especially for hard to reach organs, including the brain. There is a reduced chance of off-target effects if the CPPs are used for the nickase and nuclease versions of the Cas9 since the protein is only be present for a short period of time. Immune response could potentially be reduced since the protein may only need to be present for a very short period, and if there are adverse reactions it can clear the system, which is much more difficult with an injected virus. The CPPs also allow for tighter dosage control, or repeated injections to increase number of cells that receive the targeted endonuclease (e.g., Cas9 protein). Outside of a direct injection the CPP method also allows for seamless editing in vitro for therapies that would edit cells and then inject them back into the patient. With current viral technologies the gene editing construct remains, but if using a CPP-endonuclease construct the purified protein would eventually be depleted in the edited cells may pose less of an immune risk to a transplant patient.

Additionally the newly characterized CPPs can deliver other cargos including, but not limited to nucleic acids, making combinational treatments of Cas9 and siRNA or antisense oligonucleotides possible using the same CPP. As shown in our preliminary (see Example 1) we have characterized and purified milligram quantities of protein, tested CRISPR constructs, and measured the construct's gene editing capabilities.

Accordingly, in certain embodiments, a construct is provided that comprises a cell penetrating peptide attached to an effector that is to be delivered into a cell. In certain embodiments the cell penetrating peptide comprises a Zika cell penetrating peptide (Zika CPP). In certain embodiments the effector comprises a protein (e.g., an enzyme), a nucleic acid (e.g., DNA, RNA, ssDNA, antisense oligonucleotides, etc.), an organic compound, a nanoparticle, a viral particle, and the like. In certain embodiments the effector comprises a targeted endonuclease (e.g., a CRISPR/Cas endonuclease, a Transcription Activator-Like Effector Nuclease (TALEN), a zinc finger endonuclease, etc.).

In various embodiments methods of use of the constructs are also provided. In certain embodiments the methods of use comprising a method of transporting an effector into a cell where the method comprises contacting the cell with a construct comprising a cell penetrating peptide attached to the effector. In certain embodiments the cell is contacted with the construct ex vivo. In certain embodiments the cell is contacted with the construct by in vivo administration of the construct, e.g., to a mammal.

Cell Penetrating Peptides (CPPs)

In various embodiments compositions are provide that comprises a cell penetrating peptide attached to an effector (e.g., a protein (e.g., an enzyme), a nucleic acid (e.g., DNA, RNA, ssDNA, antisense oligonucleotides, etc.), an organic compound, a nanoparticle, a viral particle, and the like). In certain embodiments the cell penetrating peptides comprise the Zika cell penetrating peptide described herein. Without being bound to a particular theory it is believed that this CPP is previously unknown.

Zika CPP

In certain embodiments the cell penetrating peptide comprises a CPP derived from Zika virus. In certain embodiments the amino acid sequence of the "Zika CPP" comprises the sequence: ENLEYRIMLSVHGSQHSGMIVNDTG HETDENR AKVEIT PNSPR (SEQ ID NO:1) or fragments thereof that retain the ability to penetrate into cells.

In certain embodiments the cell penetrating peptide has at least 80%, or at least 85%, or at least 90%, or at least 95%, or at least 98%, or at least 99% sequence identity with the amino acid sequence of SEQ ID NO:1. In certain embodiments this CPP ranges in length up to 100 amino acids, or up to 90 amino acids, or up to 80 amino acids, or up to 70 amino acids, or up to 60 amino acids, or up to 50 amino acids, or up to 49 amino acids, or up to 48 amino acids, or up to 47 amino acids, or up to 46 amino acids, or up to 45 amino acids, or up to 44 amino acids, or up to 43 amino acids.

Effectors

In various embodiments construct are provided comprising a cell penetrating peptide (e.g., a Zika CPP.) attached to an effector that is to be delivered into a cell. In certain embodiments the effector comprises a protein (e.g., an enzyme), a nucleic acid (e.g., DNA, RNA, ssDNA, antisense oligonucleotides, transposons, etc.), an organic compound, a nanoparticle, a viral particle (e.g., the CPP is attached to or expressed as a component of a viral particle coating), and the like.

In certain embodiments, the effector comprises a protein. It is believed that essentially any protein can be delivered into a cell using one or more of the Zika cell penetrating peptides described herein. In certain embodiments the protein ranges in length from about 5 aa, or from about 10 aa, or from about 15 aa, or from about 20aa, or from about 25 aa, or from about 30 aa, or from about 35aa, or from about 40 aa, or from about 45aa, or from about 50 aa, up to about 2000aa, or up to about 1500aa, or up to about 1000 aa, or up to about 500aa, or up to about 400 aa, or up to about 300 aa, or up to about 200 aa, or up to about 100 aa, or up to about 75aa.

In certain embodiments the effector comprises a targeted endonuclease (e.g., an RNA targeted endonuclease). Illustrative targeted endonucleases include, but are not limited to CRISPR/cas endonucleases, zinc finger endonucleases, Transcription Activator-Like Effector Nuclease(s) (TALENs), and the like.

CRISPR/Cas Systems

In certain embodiments the targeting endonuclease can comprise a CRISPR/Cas endonuclease that is typically guided to a target site by one or more guide RNAs (gRNAs). CRISPR-based endonucleases are RNA-guided endonucleases derived from CRISPR/Cas systems. Bacteria and archaea have evolved an RNA-based adaptive immune system that uses CRISPR (clustered regularly interspersed short palindromic repeat) and Cas (CRISPR-associated) proteins to detect and destroy invading viruses or plasmids. CRISPR/Cas endonucleases can be programmed to introduce targeted site-specific double-strand breaks by providing target-specific synthetic guide RNAs (see, e.g., Jinek et al. (2012) Science, 337: 816-821).

In various embodiments the CRISPR-based endonuclease can be derived from a CRISPR/Cas type I, type II, type III, type V, or type VI system. Non-limiting examples of suitable CRISPR/Cas proteins include Cas3, Cas4, Cas5, Cas5e (or CasD), Cash, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cu1966, and the like.

Type II CRISPR/Cas Endonucleases Cas 9)

In certain embodiments, the CRISPR-based endonuclease is derived from a type II CRISPR/Cas system. In illustrative, but non-limiting embodiments, the CRISPR-based endonuclease is derived from a Cas9 protein. In certain embodiments the Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes,*

*Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus,* or *Acaryochloris marina.* In one specific illustrative embodiment, the CRISPR-based nuclease is derived from a Cas9 protein from *Streptococcus pyogenes.*

In general, CRISPR/Cas proteins comprise at least one RNA recognition and/or RNA binding domain. RNA recognition and/or RNA binding domains interact with the guide RNA such that the CRISPR/Cas protein is directed to a specific genomic or genomic sequence. CRISPR/Cas proteins can also comprise nuclease domains (i.e., DNase or RNase domains), DNA binding domains, helicase domains, protein-protein interaction domains, dimerization domains, as well as other domains.

In certain embodiments the CRISPR-based endonuclease used in the constructs and methods described herein can be a wild type CRISPR/Cas protein, a modified CRISPR/Cas protein, or a fragment of a wild type or modified CRISPR/Cas protein. In certain embodiments the CRISPR/Cas protein can be modified to increase nucleic acid binding affinity and/or specificity, alter an enzymatic activity, and/or change another property of the protein. For example, the CRISPR/Cas protein can be truncated to remove domains that are not essential for the function of the protein. The CRISPR/Cas protein also can be truncated or modified to optimize the activity of the protein or an effector domain fused with the CRISPR/Cas protein.

In some embodiments, the CRISPR-based endonuclease can be derived from a wild type Cas9 protein, modified forms, or fragment thereof. In other embodiments, the CRISPR-based endonuclease can be derived from a modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-strand break in DNA (see, e.g., Jinek et al. (2012) Science, 337: 816-821). In one embodiment, the CRISPR-based endonuclease is derived from a Cas9 protein and comprises two function nuclease domains, which together introduce a double-stranded break into the targeted site.

The target sites recognized by naturally occurring CRISPR/Cas systems typically having lengths of about 14-15 bp (see, e.g., Cong et al. (2013) Science, 339: 819-823). The target site has no sequence limitation except that sequence complementary to the 5' end of the guide RNA (i.e., called a protospacer sequence) is typically immediately followed by (3' or downstream) a consensus sequence. This consensus sequence is also known as a protospacer adjacent motif (or PAM). Examples of PAM include, but are not limited to, NGG, NGGNG, and NNAGAAW (wherein N is defined as any nucleotide and W is defined as either A or T). At the typical length, only about 5-7% of the target sites would be unique within a target genome, indicating that off target effects could be significant. The length of the target site can be expanded by requiring two binding events. For example, CRISPR-based endonucleases can be modified such that they can only cleave one strand of a double-stranded sequence (i.e., converted to nickases). Thus, the use of a CRISPR-based nickase in combination with two different guide RNAs would essentially double the length of the target site, while still effecting a double stranded break.

The requirement of the crRNA-tracrRNA complex in a CRISPR/Cas system can be avoided by use of an engineered "single-guide RNA" (sgRNA) that comprises the hairpin normally formed by the annealing of the crRNA and the tracrRNA (see Jinek et al. (2012) *Science* 337:816; Cong et al. (2013) Sciencexpress/10.1126/science.1231143). In *S. pyrogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing and has been useful for zebrafish embryo genomic editing in vivo (see Hwang et al. (2013) *Nat. Biotechnol.,* 31(3):227) with editing efficiencies similar to ZFNs and TALENs.

Accordingly in certain embodiments, a CRISPR/Cas endonuclease complex used in the constructs and methods described herein comprises a Cas protein and at least one to two ribonucleic acids (e.g., gRNAs) that are capable of directing the Cas protein to and hybridizing to a target motif of a target polynucleotide sequence. In some embodiments, a CRISPR/Cas endonuclease complex used in the methods described herein comprises a Cas protein and one ribonucleic acid (e.g., gRNA) that is capable of directing the Cas protein to and hybridizing to a target motif of a target polynucleotide sequence.

In some embodiments, a Cas protein comprises a core Cas protein. Illustrative Cas core proteins include, but are not limited to, Cas1, Cas2, Cas3, Cas4, Cas5, Cash, Cas7, Cas8 and Cas9. In some embodiments, a Cas protein comprises a Cas protein of an *E. coli* subtype (also known as CASS2). Illustrative Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Illustrative Cas proteins of the Ypest subtype include, but are not limited to Csy1, Csy2, Csy3, and Csy4. In some embodiments, a Cas protein comprises a Cas protein of the Nmeni subtype (also known as CASS4). Illustrative Cas proteins of the Nmeni subtype include, but are not limited to Csn1 and Csn2. In some embodiments, a Cas protein comprises a Cas protein of the Dvulg subtype (also known as CASS1). Illustrative Cas proteins of the Dvulg subtype include Csd1, Csd2, and Cas5d. In some embodiments, a Cas protein comprises a Cas protein of the Tneap subtype (also known as CASS7). Illustrative Cas proteins of the Tneap subtype include, but are not limited to, Cst1, Cst2, Cas5t. In some embodiments, a Cas protein comprises a Cas protein of the Hmari subtype. Illustrative Cas proteins of the Hmari subtype include, but are not limited to Csh1, Csh2, and Cas5h. In some embodiments, a Cas protein comprises a Cas protein of the Apern subtype (also known as CASS5). Illustrative Cas proteins of the Apern subtype include, but are not limited to Csa1, Csa2, Csa3, Csa4, Csa5, and Cas5a. In some embodiments, a Cas protein comprises a Cas protein of the Mtube subtype (also known as CASS6). Illustrative Cas proteins of the Mtube subtype include, but are not limited to Csm1, Csm2, Csm3, Csm4, and Csm5. In some embodiments, a Cas protein comprises a RAMP module Cas protein. Illustrative RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein (spCas9) or a functional portion thereof (see, e.g., UniProtKB—Q99ZW2 (CAS9_STRP1)). In some embodiments, the Cas protein is a *Staphylococcus aureus* Cas9 protein (saCas9) or a functional portion thereof. In some embodiments, the Cas protein is a *Streptococcus thermophilus* Cas9 protein (stCas9) or a functional portion thereof. In some embodiments, the Cas protein is a *Neisseria meningitides* Cas9 protein (nmCas9) or a functional portion thereof. In some embodiments, the Cas protein is a *Treponema denticola* Cas9 protein (tdCas9) or a functional portion thereof. In some embodiments, the Cas protein is Cas9 protein from any other bacterial species or functional portion thereof.

In certain embodiments the case 9 is mutated in one or more residues involved in the formation of non-specific DNA interactions. In certain embodiments such a Cas 9 comprises a mutated Cas9 such as eSpCas9 (see, e.g., Slaymaker, et al. (2016) *Science* 351: 84-88), SpCas9-HF1 (see, e.g., Kleinstiver et al. (2016) *Nature,* 529: 490-495), HypaCas9 (see, e.g., Chen et al. (2017) *Nature* 550: 407-410), and the like.

Type V and Type VI CRISPR/Cas Endonucleases

In certain embodiments the CRISPR/Cas endonuclease systems used in the constructs and methods contemplated herein include, but are not limited to a type V or type VI CRISPR/Cas endonuclease (e.g., the genome editing endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas endonuclease is C2c2. In some cases, a subject genome targeting composition includes a type V CRISPR/Cas endonuclease (e.g., Cpf1, C2c1, C2c3). In some cases, a Type V CRISPR/Cas endonuclease is a Cpf1 protein. In some cases, a subject genome targeting composition includes a type VI CRISPR/Cas endonuclease (e.g., C2c2)

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g., a chromosomal sequence) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art (see, e.g., Zetsche et al. (2015) *Cell,* 163(3):759-771; Makarova et al. (2015) *Nat. Rev. Microbiol.* 13(11): 722-736; Shmakov et al. (2015) *Mol. Cell,* 60(3):385-397; and the like).

In some cases, the Type V or type VI CRISPR/Cas endonuclease (e.g., Cpf1, C2c1, C2c2, C2c3) is enzymatically active, e.g., the Type V or type VI CRISPR/Cas protein, when bound to a guide RNA, and cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases a type V CRISPR/Cas endonuclease is a Cpf1 protein or a functional portion thereof (see, e.g., UniProtKB—A0Q7Q2 (CPF1_FRATN)). Cpf1 protein is a member of the type V CRISPR system and is a polypeptide comprising about 1300 amino acids. Cpf1 contains a RuvC-like endonuclease domain. Unlike Cas9, Cpf1 cleaves target DNA in a staggered pattern using a single ribonuclease domain. The staggered DNA double-stranded break results in a 4 or 5-nt 5' overhang.

The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see, e.g., Fagerlund et al. (2015) *Genom. Bio.* 16: 251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Accordingly, as used herein, a "CRISPR/Cas system" refers both CRISPR/Cas and/or CRISPR/Cfp1 systems, including both nuclease and/or transcription factor systems.

Accordingly, in certain embodiments the methods described herein the Cas protein isCpf1 from any bacterial species or functional portion thereof. In some aspects, Cpf1 is a *Francisella novicida* U112 protein or a functional portion thereof. In some aspects, Cpf1 is a *Acidaminococcus* sp. BV3L6 protein or a functional portion thereof. In some aspects, Cpf1 is a Lachnospiraceae bacterium ND2006 protein or a function portion thereof.

In certain embodiments, Cas protein may be a "functional portion" or "functional derivative" of a naturally occurring Cas protein, or of a modified Cas protein. A "functional derivative" of a native sequence polypeptide is a compound having a qualitative biological property in common with a native sequence polypeptide. "Functional derivatives"

include, but are not limited to, fragments of a native sequence and derivatives of a native sequence polypeptide and its fragments, provided that they have a biological activity (e.g., endonuclease activity) in common with a corresponding native sequence polypeptide. As used herein, "functional portion" refers to a portion of a Cas protein that retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional portion comprises a combination of operably linked Cpf1 protein functional domains selected from the group consisting of a DNA binding domain, at least one RNA binding domain, a helicase domain, and an endonuclease domain. In some embodiments, the functional domains form a complex. In some embodiments, a functional portion of the Cas9 protein comprises a functional portion of a RuvC-like domain. In some embodiments, a functional portion of the Cas9 protein comprises a functional portion of the HNH nuclease domain. In some embodiments, a functional portion of the Cpf1 protein comprises a functional portion of a RuvC-like domain.

In certain embodiments a biological activity contemplated herein is the ability of the functional derivative to introduce a double strand break (DSB) at a desired target site in a genomic DNA. The term "derivative" encompasses both amino acid sequence variants of polypeptide, covalent modifications, and fusions thereof. In some aspects, a functional derivative may comprise a single biological property of a naturally occurring Cas protein. In other aspects, a function derivative may comprise a subset of biological properties of a naturally occurring Cas protein.

In view of the foregoing, the term "Cas protein" as used herein encompasses a full-length Cas protein, an enzymatically active fragment of a Cas protein, and enzymatically active derivatives of a Cas protein or fragment thereof. Suitable derivatives of a Cas protein or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically, recombinantly expressed, or by a combination of these procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, a Cas protein comprises one or more amino acid substitutions or modifications. In some embodiments, the one or more amino acid substitutions comprises a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thio urea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In certain embodiments the Cas protein used in the constructs described herein may be mutated to alter functionality. Illustrative selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In certain embodiments the Cas protein (e.g., Cas9 protein) comprise truncated Cas proteins. In one illustrative, but non-limiting, embodiment, the Cas9 comprises only the domain responsible for interaction with the crRNA or sgRNA and the target DNA.

In certain embodiments the Cas proteins comprising the constructs described herein comprise a Cas protein, or truncation thereof, fused to a different functional domain. In some aspects, the functional domain is an activation or a repression domain. In other aspects, the functional domain is a nuclease domain. In some embodiments, the nuclease domain is a FokI endonuclease domain (see, e.g. Tsai (2014) Nat. Biotechnol. doi:10.1038/nbt.2908). In some embodiments, the FokI domain comprises mutations in the dimerization domain.

Guide RNA for Type II CRISPR/Cas Endonucleases Cas9 gRNA)

In various embodiments the constructs and methods described herein involve ribonucleoprotein complexes comprising a guide RNA complexed with a CRISPR endonuclease (which is attached to the cell penetrating peptide (CPP)). In certain embodiments the CRISPR/Cas endonuclease and gRNA are encoded by a single nucleic acid that is introduced into the cell (e.g., which can be attached to a CPP for introduction into a cell). In certain embodiments the CRISPR/Cas endonuclease and gRNA are introduced into the cell as a ribonucleoprotein complex (where the complex is attached to a cell penetrating peptide (e.g., a Zika PP). In certain embodiments the complex comprise a Cas protein complexed with a single guide RNA.

A nucleic acid molecule that binds to a class 2 CRISPR/Cas endonuclease (e.g., a Cas9 protein, a type V or type VI CRISPR/Cas protein, a Cpf1 protein; etc.) and targets the complex to a specific location within a target nucleic acid is referred to herein as a "guide RNA" or "CRISPR/Cas guide nucleic acid" or "CRISPR/Cas guide RNA."

In various embodiments the guide RNA provides target specificity to the complex (the RNP complex) by including a targeting segment, which includes a guide sequence (also referred to herein as a targeting sequence), which typically comprise a nucleotide sequence that is complementary to a sequence of a target nucleic acid A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules (or two segments within a single molecule): an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides and form different segments within a single RNA), and the guide RNA is referred to as a "single guide RNA", a "single-molecule guide RNA," a "one-molecule guide RNA", or simply "sgRNA." By "segment" it is meant a segment/section/region of a molecule, e.g., a contiguous stretch of nucleotides in a nucleic acid molecule. A segment can also mean a region/section of a complex such that a segment may comprise regions of more than one molecule.

In various embodiments the first segment (targeting segment) of a type II CRISPR/Cas endonuclease (e.g., a Cas9) guide RNA typically includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) the endonuclease protein. The protein-binding segment of a subject Cas9 guide RNA typically includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid. I A Cas9 guide RNA and a Cas9 protein form a complex (e.g., bind via non-covalent interactions). In certain embodiments the CPP is attached to the Cas9/gRNA ribonucleoprotein complex and effectively delivers that complex into a target cell. The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g., a target sequence in a chromosomal nucleic acid, e.g., a chromosome; a target sequence in an extrachromosomal nucleic acid, e.g., an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a type II CRISPR/Cas endonuclease guide RNA (e.g., Cas9 guide RNA) can be modified so that the guide RNA can target a CRISPR endonuclease protein to any desired sequence of any desired target nucleic acid, with the exception that the protospacer adjacent motif (PAM) sequence can be taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

In various embodiments a Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) typically comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) typically comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). In various embodiments the targeter molecule additionally provides the targeting segment. Thus, in various embodiments, a targeter and an activator molecule (as a corresponding pair) can hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) typically comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) typically comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, in various embodiments, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

In various embodiments a Cas9 guide RNA can also be said to include 3 parts: (i) a targeting sequence (a nucleotide sequence that hybridizes with a sequence of the target nucleic acid); (ii) an activator sequence (as described above) (in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g., a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter typically comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) typically comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

In various embodiments a Cas9 guide RNA (e.g., a dual guide RNA or a single guide RNA) can be comprised of any corresponding activator and targeter pair.

Targeting Segment of a Type II CRISPR Endonuclease Cas9) Guide RNA

The first segment of a subject guide nucleic acid typically includes a guide sequence (e.g., a targeting sequence)(a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

In certain embodiments the targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, in certain embodiments, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

In certain embodiments the percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Protein-Binding Segment of a Type II CRISPR Endonuclease Cas9) Guide RNA

The protein-binding segment of a Cas9 guide RNA typically interacts with a Cas9 protein. The Cas9 guide RNA guides the bound Cas9 protein to a specific nucleotide sequence within target nucleic acid via the above mentioned targeting segment. The protein-binding segment of a Cas9 guide RNA typically comprises two stretches of nucleotides that are complementary to one another and hybridize to form a double stranded RNA duplex (dsRNA duplex). Thus, the protein-binding segment can include a dsRNA duplex. In some cases, the protein-binding segment also includes stem loop 1 (the "nexus") of a Cas9 guide RNA. For example, in some cases, the activator of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "nexus"). For example, in some cases, the protein-binding segment includes stem loop 1 (the "nexus") of a Cas9 guide RNA. In some cases, the protein-binding segment includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., S. pygogenes guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "nexus"); the next stem loop is called "stem loop 2" (and is also referred to herein as the "hairpin 1"); and the next stem loop is called "stem loop 3" (and is also referred to herein as the "hairpin 2").

In some cases, a Cas9 guide RNA (sgRNA or dgRNA) (e.g., a full length Cas9 guide RNA) has stem loops 1, 2, and 3. In some cases, an activator (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loops 1, 2, and 3.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences. It will be recognized that a number of different alternative sequences can be used.

Examples of various Cas9 proteins and Cas9 guide RNAs (as well as information regarding requirements related to protospacer adjacent motif (PAM) sequences present in targeted nucleic acids) can be found in the art (see, e.g., Jinek et al. (2012) *Science,* 337(6096): 816-821; Chylinski et al. (2013) *RNA Biol.* 10(5):726-737; Ma et al., (2013) *Biomed. Res. Int.* 2013: 270805; Hou et al. (2013) *Proc. Natl. Acad. Sci. USA,* 110(39): 15644-15649; Pattanayak et al. (2013) *Nat. Biotechnol.* 31(9): 839-843; Qi et al. (2013) *Cell,* 152(5): 1173-1183; Wang et al. (2013) *Cell,* 153(4): 910-918; Chen et. al. (2013) *Nucl. Acids Res.* 41(20): e19; Cheng et. al. (2012) *Cell Res.* 23(10): 1163-1171; Cho et. al. (2013) *Genetics,* 195(3): 1177-1180; DiCarlo et al. (2013) *Nucl. Acids Res.* 41(7): 4336-4343; Dickinson et. al. (2013) *Nat. Meth.* 10(10): 1028-1034; Ebina et. al. (2013) *Sci. Rep.* 3: 2510; Fujii et. al. (2013) *Nucl. Acids Res.* 41(20): e187;

Hu et. al. (2013) *Cell Res.* 23(11): 1322-1325; Jiang et. al. (2013) *Nucl. Acids Res.* 41(20): e188; Larson et. al. (2013) *Nat. Protoc.* 8(11): 2180-2196; Mali et. at. (2013) *Nat. Meth.* 10(10): 957-963; Nakayama et. al. (2013) *Genesis*, 51(12): 835-843; Ran et. al. (2013) *Nat. Protoc.* 8(11): 2281-2308; Ran et. al. (2013) *Cell* 154(6): 1380-1389; Walsh et. al. (2013) *Proc. Natl. Acad. Sci. USA*, 110(39): 15514-15515; Yang et. al. (2013) *Cell*, 154(6): 1370-1379; Briner et al. (2014) *Mol. Cell*, 56(2): 333-339; and U.S. patents and patent applications: U.S. Pat. Nos. 8,906,616; 8,895,308; 8,889,418; 8,889,356; 8,871,445; 8,865,406; 8,795,965; 8,771,945; 8,697,359; 2014/0068797; 2014/0170753; 2014/0179006; 2014/0179770; 2014/0186843; 2014/0186919; 2014/0186958; 2014/0189896; 2014/0227787; 2014/0234972; 2014/0242664; 2014/0242699; 2014/0242700; 2014/0242702; 2014/0248702; 2014/0256046; 2014/0273037; 2014/0273226; 2014/0273230; 2014/0273231; 2014/0273232; 2014/0273233; 2014/0273234; 2014/0273235; 2014/0287938; 2014/0295556; 2014/0295557; 2014/0298547; 2014/0304853; 2014/0309487; 2014/0310828; 2014/0310830; 2014/0315985; 2014/0335063; 2014/0335620; 2014/0342456; 2014/0342457; 2014/0342458; 2014/0349400; 2014/0349405; 2014/0356867; 2014/0356956; 2014/0356958; 2014/0356959; 2014/0357523; 2014/0357530; 2014/0364333; and 2014/0377868; all of which are incorporated herein by reference in their entirety.

In certain embodiments alternative PAM sequences may also be utilized, where a PAM sequence can be NAG as an alternative to NGG (Hsu (2014) supra.) using an *S. pyogenes* Cas9. Additional PAM sequences may also include those lacking the initial G (see, e.g., Sander and Joung (2014) *Nature Biotech* 32(4):347). In addition to the *S. pyogenes* encoded Cas9 PAM sequences, other PAM sequences can be used that are specific for Cas9 proteins from other bacterial sources. For example, the PAM sequences shown below in Table 1 (adapted from Sander and Joung, supra., and Esvelt et al. (2013) *Nat. Meth.* 10(11): 1116) are specific for these Cas9 proteins:

TABLE 1

Illustrative PAM sequences from various species.

| Species | PAM | SEQ ID NO |
| --- | --- | --- |
| S. pyogenes | NGG | |
| S. pyogenes | NAG | |
| S. mutans | NGG | |
| S. thermophilius | NGGNG | 2 |
| S. thermophilius | NNAAAW | 3 |
| S. thermophilius | NNAGAA | 4 |
| S. thermophilius | NNNGATT | 5 |
| C. jejuni | NNNNACA | 6 |
| N. meningitides | NNNNGATT | 7 |
| P. multocida | GNNNCNNA | 8 |
| F. novicida | NG | |

Thus, in certain embodiments, a suitable target sequence for use with a *S. pyogenes* CRISPR/Cas system can be chosen according to the following guideline: [n17, n18, n19, or n20](G/A)G (SEQ ID NO:9). Alternatively, in certain embodiments, the PAM sequence can follow the guideline G[n17, n18, n19, n20](G/A)G (SEQ ID NO:10). For Cas9 proteins derived from non-*S. pyogenes* bacteria, the same guidelines may be used where the alternate PAMs are substituted in for the *S. pyogenes* PAM sequences.

Guide RNAs for Type V and Type VI CRISPR/Cas Endonucleases Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

In various embodiments a type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex)

In various embodiments the target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

In certain embodiments the guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

In certain embodiments the guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

In certain embodiments the duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an illustrative, but non-limiting example, a duplex-forming segment of a Cpf1 guide RNA can comprise a nucleotide sequence selected from (5' to 3'): AAUUUCUA-CUGUUGUAGAU (SEQ ID NO:11), AAUUUCUGCU-GUUGCAGAU (SEQ ID NO:12), AAUUUCCACUGUU-GUGGAU (SEQ ID NO:13), AAUUCCUACUGUUGUAGGU (SEQ ID NO:14), AAUUUCUACUAUUGUAGAU (SEQ ID NO:15), AAUUUCUACUGCUGUAGAU (SEQ ID NO:16), AAUUUCUACUUUGUAGAU (SEQ ID NO:17), AAUUUCUACUUGUAGAU (SEQ ID NO:18), and the like. The guide sequence can then follow (5' to 3') the duplex forming segment.

Examples and guidance related to type V or type VI CRISPR/Cas endonucleases and guide RNAs (as well as information regarding requirements related to protospacer adjacent motif (PAM) sequences present in targeted nucleic acids) can be found in the art (see, e.g., Zetsche et al. (2015) Cell, 163(3): 759-771; Makarova et al. (2015) Nat. Rev. Microbiol. 13(11): 722-736; Shmakov et al. (2015) Mol. Cell, 60(3): 385-397; and the like).

Modified Guide RNAs

It has been discovered that incorporation of bridged nucleic acids (BNAs) as well as locked nucleic acids (LNAs) at locations in CRISPR RNAs (crRNAs) broadly reduced off-target cleavage by the CRISPR endonuclease (e.g., Cas9). Accordingly, in certain embodiments, the guide RNAs incorporated into or used with the constructs described herein comprise one or more BNAs, and/or LNAs.

Locked Nucleic Acids.

Figure 9:
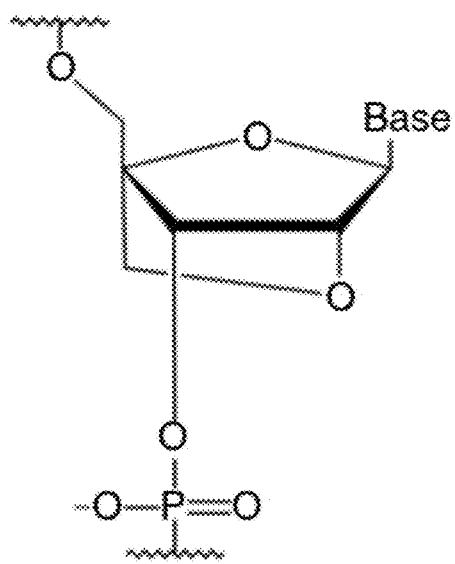
FIG. 9, panel A, illustrates the structure of LNA (2',4'-BNA), and FIG. 9, panel B illustrates the structure of $BNA^{NC}$ (2',4'-$BNA^{NC}$ [NMe]).
Figure 9:
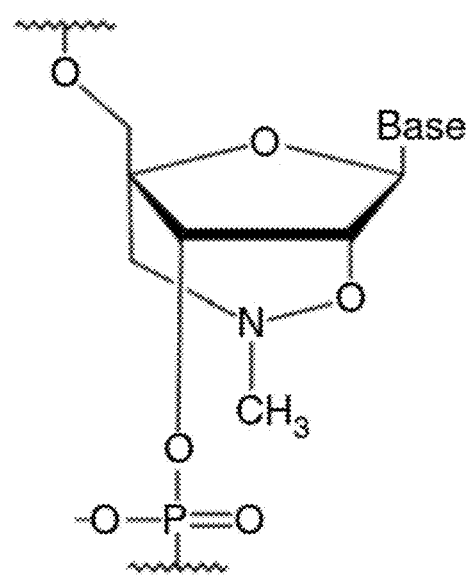

In certain embodiments the guide RNAs comprise one or more locked nucleic (LNAs) (see, e.g., FIG. 9, panel A). LNAs are conformationally restricted RNA nucleotides in which the 2' oxygen in the ribose forms a covalent bond to the 4' carbon, inducing N-type (C3'-endo) sugar puckering and a preference for an A-form helix (see, e.g., You, et al. (2006) Nucleic Acids Res. 34: e60). LNAs display improved base stacking and thermal stability compared to RNA, resulting in highly efficient binding to complementary nucleic acids and improved mismatch discrimination (see, e.g., You et al. (2006) Nucleic Acids Res. 34:e60; Vester & Wengel (2004) Biochem. 43: 13233-1324). They also display enhanced nuclease resistance (see, e.g., Vester & Wengel (2004) Biochem. 43: 13233-132429).

Accordingly, in various the guide RNAs described herein can comprise one or more LNAs. In certain embodiments the guide RNAs comprise, 1, 2, 3, 4, or more LNAs.

Bridged Nucleic Acids (BNAs).

Bridged nucleic acids (BNAs) are modified RNA nucleotides. They are sometimes also referred to as constrained or inaccessible RNA molecules. BNA monomers can contain a five-membered, six-membered or even a seven-membered bridged structure with a "fixed" $C_3$'-endo sugar puckering. The bridge is synthetically incorporated at the 2', 4'-position of the ribose to afford a 2', 4'-BNA monomer. The monomers can be incorporated into oligonucleotide polymeric structures using standard phosphoamidite chemistry. BNAs are structurally rigid oligo-nucleotides with increased binding affinities and stability.

It has been discovered that incorporation of bridged nucleic acids (BNAs) into CRSIPR guide RNAs can significantly improve CRISPR specificity. In particular, it has been demonstrated that N-methyl substituted BNAs (2',4'-$BNA^{NC}$[N-Me]) (see, e.g., FIG. 9, panel B) when incorporated into Crispr crRNAs, can improve CRISPR accuracy by as much as 10,000 times (see, e.g., Cromwell et al. (2018) Nat. Comm. 9: 1448). Accordingly, in various the guide RNAs described herein can comprise one or more BNAs. In certain embodiments the guide RNAs comprise, 1, 2, 3, 4, or more $BNA^{NC}$s.

CRISPR Interference (CRISPRi)

CRISPR interference (CRISPRi) is a genetic perturbation technique that allows for sequence-specific repression or activation of gene expression in prokaryotic and eukaryotic cells (see, e.g., Larson et al. (2013) Cell. 152(5): 1173-1183), and in various embodiments, the constructs described herein comprise a CRISPR endonuclease modified for repression or for activation of gene expression.

Repression.

CRISPRi can sterically repress transcription by blocking either transcriptional initiation or elongation. This is accomplished by designing sgRNA complementary to the promoter or the exonic sequences. The level of transcriptional repression for exonic sequences is strand-specific. sgRNA complementary to the non-template strand more strongly represses transcription compared to sgRNA complementary to the template strand. It has been suggested that this is due to the activity of helicase, which unwinds the RNA:DNA heteroduplex ahead of RNA pol II when the sgRNA is complementary to exons of the template strand.

CRISPRi can also repress transcription via an effector domain. Fusing a repressor domain to a nuclease deficient Cas (e.g., dCas9) allows transcription to be further repressed by inducing heterochromatinization. For example, the Kruppel associated box (KRAB) domain can be fused to dCas9 to effectively repress transcription of a target gene (see, e.g., Gilbert et al. (2013) *Cell,* 154(2): 442-451).

Activation.

CRISPRi can be used to activate transcription of the target gene by fusing a transcriptional activator to a nuclease deficient Cas (e.g., dCas9). For example, the transcriptional activator VP16 or VP64 can increase gene expression (see, e.g., Konermann et al. (2015) Nature, 517(7536): 583-588; and the like).

CRISPRs for Epigenetic Modification.

In certain embodiments the CRISPR construct can comprise a CRISPR modified for epigenetically modifying domains (e.g., methylation or actetylation). For example, CRISPR/cas9 can be modified for specific DNA methylation. In certain embodiments such a CRISPR/Cas 9 construct comprises a deactivated Cas9 (dCas9) nuclease and the catalytic domain of the DNA methyltransferase DNMT3A (see, e.g., Vojta et al. (2016) *Nucl. Acids Res.,* 44(12): 5615-5628).

In certain embodiments the CRISPR construct can comprise a CRISPR modified to induce histone acetylation. For example, in certain embodiments such a CRISPR/Cas 9 construct comprises a deactivated Cas9 (dCas9) nuclease and the catalytic domain of a a histone acetyltransferase (HAT) effector domain.

Zinc Finger Endonucleases.

In certain embodiments the cell penetrating peptide(s) (e.g., Zika CPP) is attached to a targeting endonuclease that comprises a zinc finger nuclease (ZFN). Typically, a zinc finger nuclease comprises a DNA binding domain (e.g., zinc finger) and a cleavage domain (e.g., nuclease), both of which are described below.

Zinc Finger Binding Domain.

Zinc finger binding domains may be engineered to recognize and bind to any nucleic acid sequence of choice (see, e.g., Beerli et al. (2002) *Nat. Biotechnol.* 20: 135-141; Pabo et al. (2001) *Ann. Rev. Biochem.* 70: 313-340; Isalan et al. (2001) *Nat. Biotechnol.* 19: 656-660; Segal et al. (2001) *Curr. Opin. Biotechnol.* 12: 632-637; Choo et al. (2000) *Curr. Opin. Struct. Biol.* 10: 411-416; Zhang et al. (2000) *J. Biol. Chem.* 275(43): 33850-33860; Doyon et al. (2008) *Nat. Biotechnol.* 26: 702-708; and Santiago et al. (2008) *Proc. Natl. Acad. Sci. USA,* 105: 5809-5814). An engineered zinc finger binding domain can have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence (see, e.g., U.S. Pat. Nos. 6,453,242 and 6,534,261, and the like). As an example, the algorithm described in U.S. Pat. No. 6,453,242 may be used to design a zinc finger binding domain to target a preselected sequence. Alternative methods, such as rational design using a nondegenerate recognition code table can also be used to design a zinc finger binding domain to target a specific sequence (see, e.g., Sera et al. (2002) *Biochemistry* 41: 7074-7081; and the like). Publically available web-based tools for identifying target sites in DNA sequences and designing zinc finger binding domains are found, inter alia, at www.zincfingertools.org and zifit.partners.org/ZiFiT/ (see also Mandell et al. (2006) *Nucl. Acids Res.* 34: W516-W523; Sander et al. (2007) *Nucl. Acids Res.* 35: W599-W605; and the like).

A zinc finger binding domain may be designed to recognize and bind a DNA sequence ranging from about 3 nucleotides to about 21 nucleotides in length, for example, from about 9 to about 18 nucleotides in length. Each zinc finger recognition region (i.e., zinc finger) typically recognizes and binds three nucleotides. In certain embodiments, the zinc finger binding domains of suitable targeted zinc finger nucleases comprise at least three zinc finger recognition regions (i.e., zinc fingers). The zinc finger binding domain, however, may comprise four, or five, or six, or more zinc finger recognition regions. A zinc finger binding domain may be designed to bind to any suitable target DNA sequence (see, e.g., U.S. Pat. Nos. 6,607,882; 6,534,261, 6,453,242, and the like.

Illustrative methods of selecting a zinc finger recognition region include, but are not limited to phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237y. In addition, enhancement of binding specificity for zinc finger binding domains has been described, for example, in WO 02/077227.

Zinc finger binding domains and methods for design and construction of fusion proteins (and polynucleotides encoding same) are known to those of skill in the art and are described in detail in U.S. Patent Application Publication Nos. 2005/0064474 and 2006/0188987. Zinc finger recognition regions and/or multi-fingered zinc finger proteins may be linked together using suitable linker sequences, including for example, linkers of five or more amino acids in length (see, e.g., U.S. Pat. Nos. 6,479,626; 6,903,185; and 7,153, 949) for non-limiting examples of linker sequences of six or more amino acids in length.

Cleavage Domain.

A zinc finger nuclease also typically includes a cleavage domain. The cleavage domain portion of the zinc finger nuclease may be obtained from any endonuclease or exonuclease. Non-limiting examples of endonucleases from which a cleavage domain may be derived include, but are not limited to, restriction endonucleases and homing endonucleases (see, e.g., New England Biolabs catalog (www.neb.com); Belfort et al. (1997) *Nucleic Acids Res.* 25:3379-3388; and the like). Additional enzymes that cleave DNA are known (e.g., 51 Nuclease; mung bean nuclease; pancreatic DNase I; micrococcal nuclease; yeast HO endonuclease). In certain embodiments one or more of these enzymes (or functional fragments thereof) may be used as a source of cleavage domains.

In certain embodiments, a cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease can comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

In various embodiments when two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs can intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other (see, e.g., U.S. Pat. Nos. 5,356,802; 5,436,150, and 5,487,994; Li et al. (1992) *Proc. Natl. Acad. Sci. USA,* 89: 4275-4279; Li et al. (1993) *Proc. Natl. Acad. Sci. USA,* 90: 2764-2768. Thus, a zinc finger nuclease can comprise the cleavage domain from at least one Type IIS restriction enzyme and one or more zinc finger binding domains, which may or may not be engineered. Illustrative type IIS restriction enzymes are described for example in International Patent Publication No: WO 07/014,275. Additional restriction enzymes also contain separable binding and cleavage domains, and these also are contemplated by the present disclosure (see, e.g., Roberts et al. (2003) *Nucleic Acids Res.* 31:418-420.

An illustrative Type IIS restriction enzyme, whose cleavage domain is separable from the binding domain, is FokI. This particular enzyme is active as a dimer (Bitinaite et al. (1998) *Proc. Natl. Acad. Sci. USA* 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, may be used to reconstitute an active enzyme dimer. Alternatively, a single polypeptide molecule containing a zinc finger binding domain and two FokI cleavage monomers can also be used.

In certain embodiments the cleavage domain may comprise one or more engineered cleavage monomers that minimize or prevent homodimerization, as described, for example, in U.S. Patent Publication Nos. 2005/0064474, 2006/0188987, 2008/0131962, and the like. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Illustrative engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499 (see, e.g., Miller et al. (2007) *Nat. Biotechnol.* 25: 778-785; Szczpek et al. (2007) *Nat. Biotechnol.* 25: 786-793). For example, the Glu (E) at position 490 may be changed to Lys (K) and the Ile (I) at position 538 may be changed to K in one domain (E490K, I538K), and the Gln (Q) at position 486 may be changed to E and the I at position 499 may be changed to Leu (L) in another cleavage domain (Q486E, I499L). In other aspects, modified FokI cleavage domains can include three amino acid changes (see, e.g., Doyon et al. (2011) *Nat. Methods,* 8: 74-81). For example, one modified FokI domain (which is termed ELD) can comprise Q486E, I499L, N496D mutations and the other modified FokI domain (which is termed KKR) can comprise E490K, I538K, H537R mutations.

In certain embodiments the Zink finger protein can be modified to have an activator, a repressor, and/or an epigenetically modifying domain (e.g., in a manner similar to modified CRISPR constructs).

Additional Domains.

In certain embodiments the zinc finger nuclease further comprises at least one nuclear localization signal or sequence (NLS). A NLS is an amino acid sequence that facilitates transport of the zinc finger nuclease protein into the nucleus of eukaryotic cells. In general, an NLS comprise a stretch of basic amino acids. Nuclear localization signals are known in the art (see, e.g., Makkerh et al. (1996) *Curr. Biol.* 6: 1025-1027; Lange et al. (2007) *J. Biol. Chem.* 282: 5101-5105). For example, in one embodiment, the NLS can be a monopartite sequence, such as PKKKRKV (SEQ ID NO:19) or PKKKRRV (SEQ ID NO:20). In another embodiment, the NLS can be a bipartite sequence. In still another embodiment, the NLS can be KRPAATKKAGQAKKKK (SEQ ID NO:21). In various embodiments the NLS can be located at the N-terminus, the C-terminus, or in an internal location of the zinc finger nuclease.

TALENs

In certain embodiments the cell penetrating peptide(s) (e.g., Zika CPP) is attached to a targeting endonuclease that comprises a Transcription Activator-Like Effector Nuclease (TALEN). TAL effector nucleases are a class of sequence-specific nucleases derived from *Xanthomonas* bacteria, that can be used to make double-strand breaks at specific target sequences in the genome of a prokaryotic or eukaryotic organism. The DNA binding domain of the TAL effector contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence.

TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences (see, e.g., WO 2010/079430; Morbitzer et al. (2010) *Proc. Natl. Acad. Sci. USA,* 107(50): 21617-21622; Scholze & Boch (2010) *Virulence,* 1: 428-432; Christian et al. (2010) *Genetics,* 186:757-761; Li et al. (2010) *Nucl. Acids Res.* (1):359-372; and Miller et al. (2011) *Nat. Biotechl.* 29: 143-148).

To produce a TALEN, a TAL protein is fused to a nuclease, which is typically a wild-type or mutated FokI endonuclease. Several mutations to FokI have been made for its use in TALENs. These, for example, improve cleavage specificity or activity (see, e.g., Cermak et al. (2011) *Nucl. Acids Res.* 39: e82; Miller et al. (2011) *Nat. Biotech.* 29:

143-148; Hockemeyer et al. (2011) *Nat. Biotech.* 29: 731-734; Wood et al. (2011) *Science,* 333: 307; Doyon et al. (2010) *Nat. Meth.* 8: 74-79; Szczepek et al. (2007) *Nat. Biotech.* 25: 786-793; and Guo et al. (2010) *J. Mol. Biol.* 200: 96).

The FokI domain functions as a dimer, typically requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity (see, e.g., Miller et al. (2011) *Nat. Biotech.,* 29: 143-148).

Examples of suitable TAL nucleases, and methods for preparing suitable TAL nucleases, are disclosed, e.g., in US Patent Application Nos. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1. In various embodiments, TAL effector nucleases are engineered that cut in or near a target nucleic acid sequence in, e.g., a genomic locus of interest, where the target nucleic acid sequence is at or near a sequence to be modified by a targeting vector. In various embodiments, the TAL nucleases suitable for use with the various methods and compositions provided herein include those that are specifically designed to bind at or near target nucleic acid sequences to be modified, e.g., by targeting vectors.

In one illustrative, but non-limiting embodiment, each monomer of the TALEN comprises 10 or more DNA binding repeats, and in some cases 15 or more DNA binding repeats (e.g., in certain embodiments, 12-25 TAL repeats), wherein each TAL repeat binds a 1 bp subsite. In one embodiment, the nuclease agent is a chimeric protein comprising a TAL repeat-based DNA binding domain operably linked to an independent nuclease. In one embodiment, the independent nuclease is a FokI endonuclease (see e.g., Kim et al. (1996) *Proc. Natl. Acad. Sci. USA,* 93:1156-1160), however, other useful endonucleases may include, but are not limited to, for example, HhaI, HindIII, NoI, BbvCI, EcoRI, BglI, and AlwI.

In some embodiments, the TAL effector domain that binds to a specific nucleotide sequence within the target DNA comprises a plurality of repeat variable-diresidues (RVD) each of which determines recognition of a base pair in the target DNA sequence, where each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

If the genome editing endonuclease to be utilized is a TALEN, in some embodiments, optimal target sites may be selected in accordance with the methods described by Sanjana et al. (2012) *Nat. Protocol.,* 7: 171-192, which is hereby incorporated by reference in its entirety. In brief, in various embodiments, TALENs function as dimers, and a pair of TALENs, referred to as the left and right TALENs, target sequences on opposite strands of DNA. TALENs can be engineered as a fusion of the TALE DNA-binding domain and a monomeric FokI catalytic domain. In certain embodiments to facilitate FokI dimerization, the left and right TALEN target sites can be chosen with a spacing of approximately 14-20 bases. Therefore, for a pair of TALENs, each targeting 20-, bp sequences, an optimal target site can have the form 5'-$TN^{19}N^{14-20}N^{19}A$-3', where the left TALEN targets 5'-$TN^{19}$-3' and the right TALEN targets the antisense strand of 5'-$N^{19}A$-3' (N=A, G, T or C). This is of course illustrative and non-limiting and examples of TALENs that bind to particular target sites are well known to those of skill in the art. For more information on TALENs, refer to U.S. Pat. No. 8,685,737, which is hereby incorporated by reference in its entirety.

In certain embodiments the TALEs can be modified to have an activator, a repressor, and/or an epigenetically modifying domain (e.g., in a manner similar to modified CRISPR constructs).

Nucleic Acid Effectors.

In certain embodiments the effector attached to the cell penetrating peptide comprises a nucleic acid. Illustrative nucleic acid effectors include, but are not limited to DNA, RNA, ssDNA, antisense oligonucleotides, RNAi molecules, gRNAs, transposons, and the like.

In certain embodiments the CPP can be used to effectively deliver a guide RNA independent of the Cas9 protein into a cell.

It is believed that essentially any nucleic acid can be delivered into a cell using one or more of the Zika CPPs described herein. In certain embodiments the nucleic acid ranges in length from about 5 nt (or bp) up to about 6,000 nt (or bp). In certain embodiments the nucleic acid ranges in length from about 8, or from about 10, or from about 15, or from about 20 up to about 6,000, or up to about 5,000, or up to about 4,000, or up to about 3,000, or up to about 2,000, or up to about 1,000, or up to about 500, or up to about 100 nt (bp).

Nanoparticle Effectors.

In certain embodiments the effector attached to the cell penetrating peptide comprises a nanoparticle. Illustrative nanoparticles include, but are not limited to polymeric nanoparticles, mesoporous silica nanoparticles, alginate nanoparticles, and the like that can optionally be loaded with one or more therapeutic agents.

The foregoing effectors are illustrative and non-limiting. Using the teaching provided herein, numerous other effectors can be attached to the CPPs described herein for effective delivery into a cell.

Viral Effectors.

In certain embodiments the effector attached to the cell penetrating peptide comprises a viral particle. Illustrative viral particles include, but are not limited to adenovirus particles, adeno-associated virus (AAV) particles, lentiviral (LV) particles and the like.

In certain embodiments the CPP is chemically conjugated to the viral particle. In other embodiments, the CPP can be expressed as (displayed on) the viral coating. Methods of expressing heterologous proteins on viral coatings (e.g., capsids) are well known to those of skill in the art (see, e.g., U.S. Pat. No. 6,204,059 B1; Jurgens et al. (2012) *J. Virol.,* 86(1): 246-261; and the like).

Attaching the Cell Penetrating Peptide (CPP) to the Effector (e.g., a Cas Protein).

In certain embodiments the cell penetrating peptide (e.g., Zika CPP) can be attached to the effector directly (e.g., through a covalent or non-covalent linkage), or through a linker (e.g., a peptide linker, or a non-peptide linker), or through an amino acid or other functional group.

In certain embodiments multiple cell penetrating peptides (CPPs) can be attached to a single effector. In certain embodiments, multiple effectors can be attached to a CPP. In certain embodiments a single CPP is attached to a single effector.

Methods of coupling the cell penetrating peptide (e.g., Zika CPP) to the effector (e.g., a complex comprising a CRISPR/Cas endonuclease and a guide RNA) are well known to those of skill in the art. Examples include, but are not limited to the use of biotin and avidin or streptavidin (see, e.g., U.S. Pat. No. 4,885,172 A), typical biotin/avidin alternatives (e.g., FITC/anti-FITC (see, e.g., Harmer and Samuel (1989) *J. Immunol. Meth.* 122(1): 115-221), dioxigenin/anti-dioxigenin, and the like), by traditional chemical conjugation using, for example, bifunctional coupling agents such as glutaraldehyde, diimide esters, aromatic and aliphatic diisocyanates, bis-p-nitrophenyl esters of dicarboxylic acids, aromatic disulfonyl chlorides and bifunctional arylhalides such as 1,5-difluoro-2,4-dinitrobenzene; p,p'-difluoro m,m'-dinitrodiphenyl sulfone, sulfhydryl-reactive maleimides, and the like. In certain embodiments, where the effector comprises a protein, the effector can be expressed as a fusion protein with the cell penetrating peptide (e.g., Zika CPP). In such instances, the fusion can be directly between the effector (e.g., Cas endonuclease), or through an intervening amino acid, or through a peptide linker. In certain embodiments the peptide linker, when present, can be an enzymatically cleavable peptide linker.

As noted above, in certain embodiments the cell penetrating peptide (e.g., Zika CPP) is attached to the effector (e.g., Cas endonuclease) via a linker (linking agent). A "linker" or "linking agent" as used herein, is a molecule that is used to join two or more molecules. In certain embodiments, the linker is typically capable of forming covalent bonds to both molecule(s) (e.g., the cell penetrating peptide (e.g., Zika CPP) and the Cas endonuclease). Suitable linkers are well known to those of skill in the art and include, but are not limited to, straight or branched-chain carbon linkers, heterocyclic carbon linkers, or peptide linkers. In certain embodiments, the linkers can be joined to the constituent amino acids through their side groups (e.g., through a disulfide linkage to cysteine) as noted above, while in other embodiments, the linkers will be joined to the alpha carbon amino and carboxyl groups of the terminal amino acids when such are present.

Typically the linker comprises a functional group that is reactive with a corresponding functional group on the cell penetrating peptide (e.g., Zika CPP) and/or the effector (e.g., Cas endonuclease). A bifunctional linker has one functional group reactive with a group on the cell penetrating peptide (e.g., Zika CPP) and another functional group reactive on the effector (e.g., Cas endonuclease) and can be used to form the desired conjugate. A heterobifunctional linker typically comprises two or more different reactive groups that react with sites on the cell penetrating peptide (e.g., Zika CPP) and on the effector (e.g., Cas endonuclease), respectively. For example, a heterobifunctional crosslinker such as cysteine may comprise an amine reactive group and a thiol-reactive group can interact with an aldehyde on a derivatized peptide. Additional combinations of reactive groups suitable for heterobifunctional crosslinkers include, for example, amine- and sulfhydryl reactive groups; carbonyl and sulfhydryl reactive groups; amine and photoreactive groups; sulfhydryl and photoreactive groups; carbonyl and photoreactive groups; carboxylate and photoreactive groups; and arginine and photoreactive groups.

Such reactions and functional groups are illustrative and non-limiting. Other illustrative suitable reactive groups include, but are not limited to thiol (—SH), carboxylate (COOH), carboxyl (—COOH), carbonyl, amine ($NH_2$), hydroxyl (—OH), aldehyde (—CHO), alcohol (ROH), ketone ($R_2CO$), active hydrogen, ester, sulfhydryl (SH), phosphate (—$PO_3$), or photoreactive moieties. Amine reactive groups include, but are not limited to e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, but are not limited to e.g., haloacetyl and alkyl halide derivates, maleimides, aziridines, acryloyl derivatives, arylating agents, and thiol-disulfides exchange reagents. Carboxylate reactive groups include, but are not limited to e.g., diazoalkanes and diazoacetyl compounds, such as carbonyldiimidazoles and carbodiimides. Hydroxyl reactive groups include, but are not limited to e.g., epoxides and oxiranes, carbonyldiimidazole, oxidation with periodate, N,N'-disuccinimidyl carbonate or N-hydroxylsuccinimidyl chloroformate, enzymatic oxidation, alkyl halogens, and isocyanates. Aldehyde and ketone reactive groups include, but are not limited to e.g., hydrazine derivatives for schiff base formation or reduction amination. Active hydrogen reactive groups include, but are not limited to e.g., diazonium derivatives for mannich condensation and iodination reactions. Photoreactive groups include, but are not limited to e.g., aryl azides and halogenated aryl azides, benzophenones, diazo compounds, and diazirine derivatives.

In certain embodiments, the linker comprises a cleavable linker. Cleavable linkers include both chemically cleavable linkers and enzymatically cleavable linkers.

A number of different chemically cleavable linkers are known to those of skill in the art (see, e.g., U.S. Pat. Nos. 4,618,492; 4,542,225, and 4,625,014). Illustrative chemically cleavable linkers include, but are not limited to, acid-labile linkers, disulfide linkers, and the like. Acid-labile linkers are designed to be stable at pH levels encountered in the blood, but become unstable and degrade when the low pH environment in lysosomes is encountered. Acid-sensitive linkers include, but are not limited to hydrazones, acetals, cis-aconitate-like amides, and silyl ethers (see, e.g., Perez et al. (2013) *Drug Discov. Today,* 1-13). Hydrazones are easily synthesized and have a plasma half-life of 183 hours at pH 7 and 4.4 hours at pH 5, indicating that they are selectively cleavable under acidic conditions such as those found in the lysosome (see, e.g., Doronina et al. 92013) *Nat. Biotechnol.* 21(7): 778-784).

Disulfide bridges are cleavable linkers that take advantage of the cellular reducing environment (see, e.g., Saito et al. (2013) *Adv. Drug Deliv. Rev.* 55(2): 199-215). After internalization and degradation, disulfide bridges can release drugs in the lysosome.

Enzymatically cleavable linkers are selected to be cleaved by an enzyme (e.g., a protease). Protease-cleavable linkers are typically designed to be stable in blood/plasma, but are rapidly cleaved in lysosomes by lysosomal enzymes. The most popular enzymatic cleavage sequence is the dipeptide valine-citrulline, combined with a self-immolative linker p-aminobenzyl alcohol (PAB). Cleavage of an amide-linked PAB triggers a 1,6-elimination of carbon dioxide and concomitant release of the free drug in parent amine form (see, e.g., Burke et al. (2009) *Bioconjug. Chem.* 20(6): 1242-1250).

A library of dipeptide linkers was screened by Debowchik and co-workers to measure the rate of doxorubicin release by enzymatic hydrolysis (see, e.g., Dubowchik et al. (2002) *Bioconjug. Chem.* 13(4): 855-869; Dubowchik et al. (2002) *Bioorg. Med. Chem. Lett.* 12(11): 1529-1532). They found that Phe-Lys was cleaved most rapidly with a half-life of 8 min, followed closely by Val-Lys with a half-life of 9 min. In stark contrast, Val-Cit showed a half-life of 240 min. They also found that removal of the PAB group reduced the cleavage rate, presumably through steric interference with enzyme binding.

Another study compared the potency of auristatin derivative MMAE linked by dipeptide linkers Phe-Lys and Val-Cit and an analogous hydrazone linker. The Val-Cit linker proved to be over 100 times as stable as the hydrazone linker in human plasma. Most significantly, the Phe-Lys linker was substantially less stable than Val-Cit in human plasma, which accounts for its current popularity (see, e.g., Doronina et al. (2003) *Nat. Biotechnol.* 21(7): 778-784).

Non-peptide enzymatically cleavable linkers are also known to those of skill in the art. A glucuronide linker incorporates a hydrophilic sugar group that is cleaved by the lysosomal enzyme beta glucuronidase. Once the sugar is cleaved from the phenolic backbone, self-immolation of the PAB group releases the conjugated moiety (see, e.g., Jeffrey et al. (3006) *Bioconjug. Chem.* 17(3): 831-840).

Many procedures and linker molecules for attachment of various molecules to peptides or proteins are known (see, e.g., European Patent Application No. 188,256; U.S. Pat. Nos. 4,671,958, 4,659,839, 4,414,148, 4,699,784; 4,680, 338; 4,569,789; and 4,589,071; and Borlinghaus et al. (1987) *Cancer Res.* 47: 4071-4075). Illustrative non-peptide linkers suitable for chemical conjugation are shown in Table 2.

Fusion Proteins.

In certain embodiments where the effector comprise a protein, the effector can be fused directly to cell penetrating peptide (CPP), fused through an amino acid, or fused through a peptide linker. In certain embodiments the CPP attached to the protein effector (e.g., Cas endonuclease) is simply synthesized directly using methods of chemical peptide synthesis.

In certain embodiments, the CPP attached to the protein effector (e.g., Cas endonuclease) can be recombinantly expressed as a fusion protein (e.g., directly fused, joined through an amino acid, or joined through a linker). Generally this involves creating a DNA sequence that encodes the fusion protein, placing the DNA in an expression cassette under the control of a particular promoter, expressing the protein in a host, isolating the expressed protein and, if required, renaturing the protein.

DNA encoding the fusion proteins can be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; and the solid support method of U.S. Pat. No. 4,458,066.

Chemical synthesis produces a single stranded oligonucleotide. This can be converted into double stranded DNA by hybridization with a complementary sequence or by polymerization with a DNA polymerase using the single strand as a template. One of skill would recognize that while chemical synthesis of DNA is limited to sequences of about 100 bases, longer sequences can be obtained by the ligation of shorter sequences.

Alternatively, subsequences can be cloned and the appropriate subsequences cleaved using appropriate restriction enzymes. The fragments can then be ligated to produce the desired DNA sequence.

In certain embodiments, DNA encoding fusion proteins constructs described herein may be cloned using DNA amplification methods such as polymerase chain reaction (PCR). Thus, for example, the nucleic acid sequence encoding the guided endonuclease (e.g., Cas9) can be PCR amplified, using a sense primer containing the restriction site for NdeI and an antisense primer containing the restriction site for HindIII. This produces a nucleic acid encoding the endonuclease and having terminal restriction sites. Similarly the nucleic acid encoding the cell penetrating peptide (CPP) can be provided having complementary restriction sites. Ligation of sequences and insertion into a vector produces a vector encoding the fusion protein.

As noted above, while the cell penetrating peptide (e.g., Zika CPP) and protein effector (e.g., Cas endonuclease) can be directly joined together, one of skill will appreciate that they can be separated by linker consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity. In certain embodiments the linker may comprise an enzymatic cleavage site.

The nucleic acid sequences encoding the fusion proteins can be expressed in a variety of host cells, including *E. coli* (as described in Example 1), other bacterial hosts, yeast, and various higher eukaryotic cells such as the COS, CHO and HeLa cells lines and myeloma cell lines. The recombinant protein gene will be operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The plasmids can be transferred into the chosen host cell by well-known methods such as calcium chloride transformation for *E. coli* and calcium phosphate treatment or electroporation for mammalian cells. Cells transformed by the plasmids can be selected by resistance to antibiotics conferred by genes contained on the plasmids, such as the amp, gpt, neo and hyg genes.

Once expressed, the recombinant fusion proteins can be purified according to standard procedures of the art, including ammonium sulfate precipitation, affinity columns, column chromatography, gel electrophoresis and the like (see, generally, R. Scopes (1982) *Protein Purification*, Springer-Verlag, N.Y.; Deutscher (1990) *Methods in Enzymology Vol. 182: Guide to Protein Purification.*, Academic Press, Inc. N.Y.). Substantially pure compositions of at least about 90 to 95% homogeneity are preferred, and 98 to 99% or more homogeneity are most preferred for pharmaceutical uses. Once purified, partially or to homogeneity as desired, the polypeptides may then be used therapeutically.

One of skill in the art would recognize that after chemical synthesis, biological expression, or purification, the fusion protein may possess a conformation substantially different than the native conformations of the constituent polypeptides. In this case, it may be necessary to denature and reduce the polypeptide and then to cause the polypeptide to re-fold into the preferred conformation. Methods of reducing and denaturing proteins and inducing re-folding are well known to those of skill in the art (See, Debinski et al. (1993) *J. Biol. Chem.*, 268: 14065-14070; Kreitman and Pastan (1993) *Bioconjug. Chem.*, 4: 581-585; and Buchner, et al. (1992) *Anal. Biochem.*, 205: 263-270).

One of skill would recognize that modifications can be made to the fusion proteins without diminishing their biological activity. Some modifications may be made to facilitate the cloning, expression, or incorporation of the CPP and/or the protein effector into a fusion protein. Such modifications are well known to those of skill in the art and include, for example, a methionine added at the amino terminus to provide an initiation site, or additional amino acids placed on either terminus to create conveniently located restriction sites or termination codons.

As indicated above, in various embodiments an amino acid, or a peptide linker is used to join the cell penetrating peptide (e.g., Zika CPP) to the protein effector (e.g., Cas endonuclease). In various embodiments the peptide linker is relatively short, typically about 20 amino acids or less or about 15 amino acids or less or about 10 amino acids or less or about 8 amino acids or less or about 5 amino acids or less or about 3 amino acids or less, or is a single amino acid. Suitable illustrative linkers include, but are not limited to the amino acids or peptide linkers shown in Table 2.

TABLE 2

Illustrative peptide and non-peptide linkers.

| Linker | SEQ ID NO: |
|---|---|
| A | |
| R | |
| N | |
| D | |
| B | |
| C | |
| E | |
| Q | |
| Z | |
| G | |
| H | |
| I | |
| L | |
| K | |
| M | |
| F | |
| P | |
| S | |
| T | |
| W | |
| Y | |
| V | |
| AAA | |
| GGG | |
| SGG | |
| SAT | |
| PYP | |
| ASA | |

TABLE 2-continued

Illustrative peptide and non-peptide linkers.

| Linker | SEQ ID NO: |
|---|---|
| GGGG | 22 |
| PSGSP | 23 |
| PSPSP | 24 |
| KKKK | 25 |
| RRRR | 26 |
| ASASA | 27 |
| GGSGGS | 28 |
| GGGGS | 29 |
| GGGGS GGGGS | 30 |
| GGGGS GGGGS GGGGS | 31 |
| GGGGS GGGGS GGGGS GGGGS | 32 |
| GGGGS GGGGS GGGGS GGGGS GGGGS | 33 |
| GGGGS GGGGS GGGGS GGGGS GGGGS GGGGS | 34 |
| GGGGS GGGGS GGGGS FK GGGGS GGGGS GGGGS | 35 |
| GGGGS GGGGS GGGGS VA GGGGS GGGGS GGGGS | 36 |
| 2-nitrobenzene or O-nitrobenzyl | |
| Nitropyridyl disulfide | |
| Dioleoylphosphatidylethanolamine (DOPE) | |
| S-acetylmercaptosuccinic acid | |
| 1,4,7,10-tetraazacyclododecane-1,4,7,10-tetracetic acid (DOTA) | |
| β-glucuronide and β-glucuronide variants | |
| Poly(alkylacrylic acid) | |
| Benzene-based linkers (for example: 2,5-Bis(hexyloxy)-1,4-bis[2,5-bis(hexyloxy)-4-formyl-phenylenevinylene]benzene) and like molecules | |
| Disulfide linkages | |
| Poly(amidoamine) or like dendrimers linking multiple target and killing peptides in one molecule | |
| Hydrazone and hydrazone variant linkers | |
| PEG of any chain length | |
| Succinate, formate, acetate butyrate, other like organic acids | |
| Aldols, alcohols, or enols | |
| Peroxides | |
| alkane or alkene groups of any chain length | |
| Variants of any of the above linkers containing halogen or thiol groups | |
| Quaternary-ammonium-salt linkers | |
| Allyl(4-methoxyphenyl)dimethylsilane | |

TABLE 2-continued

Illustrative peptide and non-peptide linkers.

| Linker | SEQ ID NO: |
|---|---|
| 6-(Allyloxycarbonylamino)-1-hexanol | |
| 3-(Allyloxycarbonylamino)-1-propanol | |
| 4-Aminobutyraldehyde diethyl acetal | |
| (E)-N-(2-Aminoethyl)-4-{2-[4-(3-azidopropoxy)phenyl]diazenyl}benzamide hydrochloride | |
| N-(2-Aminoethyl)maleimide trifluoroacetate | |
| Amino-PEG4-alkyne | |
| Benzyl N-(3-hydroxypropyl)carbamate | |
| 4-(Boc-amino)-1-butanol | |
| 4-(Boc-amino)butyl bromide | |
| 2-(Boc-amino)ethanethiol | |
| 2-[2-(Boc-amino)ethoxy]ethoxyacetic acid (dicyclohexylammonium) salt | |
| 2-(Boc-amino)ethyl bromide | |
| 6-(Boc-amino)-1-hexanol | |
| 21-(Boc-amino)-4,7,10,13,16,19-hexaoxaheneicosanoic acid | |
| 6-(Boc-amino)hexyl bromide | |
| 5-(Boc-amino)-1-pentanol | |
| 3-(Boc-amino)-1-propanol | |
| 3-(Boc-amino)propyl bromide | |
| 15-(Boc-amino)-4,7,10,13-tetraoxapentadecanoic acid | |
| N-Boc-1,4-butanediamine | |
| N-Boc-cadaverine | |
| N-Boc-ethanolamine | |
| N-Boc-ethylenediamine | |
| N-Boc-2,2'-(ethylenedioxy)diethylamine | |
| N-Boc-1,6-hexanediamine | |
| N-Boc-1,6-hexanediamine hydrochloride | |
| N-Boc-4-isothiocyanatoaniline | |
| N-Boc-4-isothiocyanatobutylamine | |
| N-Boc-2-isothiocyanatoethylamine | |
| N-Boc-3-isothiocyanatopropylamine | |
| N-Boc-N-methylethylenediamine | |
| N-Boc-m-phenylenediamine | |
| N-Boc-p-phenylenediamine | |
| 2-(4-Boc-1-piperazinyl)acetic acid | |
| N-Boc-1,3-propanediamine | |
| N-Boc-N'-succinyl-4,7,10-trioxa-1,13-tridecanediamine | |
| N-Boc-4,7,10-trioxa-1,13-tridecanediamine | |

TABLE 2-continued

Illustrative peptide and non-peptide linkers.

| Linker | SEQ ID NO: |
|---|---|
| N-(4-Bromobutyl)phthalimide | |
| 4-Bromobutyric acid | |
| 4-Bromobutyryl chloride purum | |
| 4-Bromobutyryl chloride | |
| N-(2-Bromoethyl)phthalimide | |
| 6-Bromo-1-hexanol | |
| 3-(Bromomethyl)benzoic acid N-succinimidylester | |
| 4-(Bromomethyl)phenyl isothiocyanate | |
| 8-Bromooctanoic acid | |
| 8-Bromo-1-octanol | |
| 4-(2-Bromopropionyl)phenoxyacetic acid | |
| N-(3-Bromopropyl)phthalimide | |
| 4-(tert-Butoxymethyl)benzoic acid | |
| tert-Butyl 2-(4-{[4-(3-azidopropoxy)phenyl]azo}benzamido)ethylcarbamate | |
| 2[2-(tert-Butyldimethylsilyloxy)ethoxy]ethanamine | |
| tert-Butyl 4-hydroxybutyrate | |
| 4-(2-Chloropropionyl)phenylacetic acid | |
| 1,11-Diamino-3,6,9-trioxaundecane | |
| di-Boc-cystamine | |
| Diethylene glycol monoallyl ether | |
| 3,4-Dihydro-2H-pyran-2-methanol | |
| 4-[(2,4-Dimethoxyphenyl)(Fmoc-amino)methyl]phenoxyacetic acid | |
| 4-(Diphenylhydroxymethyl)benzoic acid | |
| 4-(Fmoc-amino)-1-butanol | |
| 2-(Fmoc-amino)ethanol | |
| 2-[2-(Fmoc-amino)ethoxy]ethylamine hydrochloride | |
| 2-(Fmoc-amino)ethyl bromide | |
| 6-(Fmoc-amino)-1-hexanol | |
| 5-(Fmoc-amino)-1-pentanol | |
| 3-(Fmoc-amino)-1-propanol | |
| 3-(Fmoc-amino)propyl bromide | |
| N-Fmoc-2-bromoethylamine | |
| N-Fmoc-1,4-butanediamine hydrobromide | |
| N-Fmoc-cadaverine hydrobromide | |
| N-Fmoc-ethylenediamine hydrobromide | |
| N-Fmoc-1,6-hexanediamine hydrobromide | |
| N-Fmoc-1,3-propanediamine hydrobromide | |

TABLE 2-continued

Illustrative peptide and non-peptide linkers.

| Linker | SEQ ID NO: |
|---|---|
| N-Fmoc-N"-succinyl-4,7,10-trioxa-1,13-tridecanediamine | |
| (3-Formyl-1-indolyl)acetic acid | |
| 6-Guanidinohexanoic acid | |
| 4-Hydroxybenzyl alcohol | |
| N-(4-Hydroxybutyl)trifluoroacetamide | |
| 4'-Hydroxy-2,4-dimethoxybenzophenone | |
| N-(2-Hydroxyethyl)maleimide | |
| 4-[4-(1-Hydroxyethyl)-2-methoxy-5-nitrophenoxy]butyric acid | |
| N-(2-Hydroxyethyl)trifluoroacetamide | |
| N-(6-Hydroxyhexyl)trifluoroacetamide | |
| 4-Hydroxy-2-methoxybenzaldehyde | |
| 4-Hydroxy-3-methoxybenzyl alcohol | |
| 4-(Hydroxymethyl)benzoic acid | |
| 4-(4-Hydroxymethyl-3-methoxyphenoxy)butyric acid | |
| 4-(Hydroxymethyl)phenoxyacetic acid | |
| 3-(4-Hydroxymethylphenoxy)propionic acid | |
| N-(5-Hydroxypentyl)trifluoroacetamide | |
| 4-(4'-Hydroxyphenylazo)benzoic acid | |
| N-(3-Hydroxypropyl)trifluoroacetamide | |
| 2-Maleimidoethyl mesylate technical | |
| 4-Mercapto-1-butanol | |
| 6-Mercapto-1-hexanol | |
| Phenacyl 4-(bromomethyl)phenylacetate | |
| 4-Sulfamoylbenzoic acid | |
| N-Trityl-1,2-ethanediamine hydrobromide | |
| 4-(Z-Amino)-1-butanol | |
| 6-(Z-Amino)-1-hexanol | |
| 5-(Z-Amino)-1-pentanol | |
| N-Z-1,4-Butanediamine hydrochloride | |
| N-Z-Ethanolamine | |
| N-Z-Ethylenediamine hydrochloride | |
| N-Z-1,6-hexanediamine hydrochloride | |
| N-Z-1,5-pentanediamine hydrochloride | |
| N-Z-1,3-Propanediamine hydrochloride | |
| 1,4-Bis[3-(2-pyridyldithio)propionamido]butane | |
| BMOE (bis-maleimidoethane) | |
| BM(PEG)2 (1,8-bismaleimido-diethyleneglycol) | |
| BM(PEG)3 (1,11-bismaleimido-triethyleneglycol) | |

TABLE 2-continued

Illustrative peptide and non-peptide linkers.

| Linker | SEQ ID NO: |
|---|---|
| DTME (dithio-bis-maleimidoethane) | |
| BMOE (bis-maleimidoethane) | |
| Maleimidoacetic acid N-hydroxysuccinimide ester | |
| 4-(N-Maleimidomethyl)cyclohexanecarboxylic acid N-hydroxysuccinimide ester | |
| 4-(N-Maleimidomethyl)cyclohexane-1-carboxylic acid 3-sulfo-N-hydroxysuccinimide ester | |
| 4-(4-Maleimidophenyl)butyric acid N-hydroxysuccinimide ester | |
| 3-(Maleimido)propionic acid N-hydroxysuccinimide ester | |

(All amino-acid-based linkers could be L, D, combinations of L and D forms, (3-form, and the like).

The foregoing methods of attaching cell penetrating peptides (e.g., Zika CPP) to an effector are illustrative and not limiting. Using the teaching provided herein, numerous other attachment strategies and/or linkers will be available to one of skill in the art.

Methods of Use.

In various embodiments methods of use of the constructs described herein are provided. In certain embodiments the methods comprise of delivering an effector into a cell where the method involves contacting the cell (target/host cell) with a construct as described herein comprising a cell penetrating peptide (CPP) attached to the effector. In certain embodiments the construct is contacted to said cell ex vivo. In certain embodiments the cell comprises a cell from a cell line. In certain embodiments the cell comprises a neuronal cell. In certain embodiments the cell comprises a stem cell (e.g., an adult stem cell, an embryonic stem cell, a cord blood stem cell, a peripheral blood stem cell (PBSC), and an induced pluripotent stem cell, etc.).

In certain embodiments the construct is contacted to the cell in vivo. In certain embodiments the contacting comprises administering the construct to a mammal (e.g., to a human, or to a non-human mammal). In certain embodiments the construct delivers the effector to a neural tissue (e.g., brain/CNS, or peripheral nervous system) in the mammal. In certain embodiments the construct delivers the construct to essentially any other desired target organ/tissue (e.g., liver, kidney, etc.).

Kits.

In various embodiments kits are provided for practice, inter alia, of the methods described herein. In certain embodiments the kits comprise a container containing a construct as described herein (e.g., a construct comprising a cell penetrating peptide attached to an effector). In certain embodiments, particularly where the effector comprising the construct is a targeted endonuclease, the kit can additionally include one or more guide RNAs, e.g., as described herein. In certain embodiments the guide RNA is provided as a component of a ribonucleoprotein complex formed from the guide RNA and the endonuclease comprising the construct. In certain embodiments the guide RNA is provided separate from the complex, e.g., in a separate container, or in the same container as a separate construct. In certain embodiments the guide RNA is provided as a component of a vector (e.g., as an adenoviral (AV) vector, an adeno-associated virus (AAV) vector, as a lentiviral (LV) vector, and the like.

In certain embodiments the kit comprises instructions (instructional materials) for using the kit for delivering one or more "effectors" (e.g., CRISPR/Cas endonuclease) to target cells, organs, or tissues.

While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

The following examples are offered to illustrate, but not to limit the claimed invention.

Example 1

We have produced one new cell penetrating peptides attached to Cas9 proteins using sequences from the Zika virus. The Zika derived CPP is completely novel. Zika CPP-Cas9 constructs were delivered into various cell types including, but not limited to, SHSYSY cells, neural stem cells, mouse striatal cells and in vivo mouse brain and other tissues, and the retained intracellular functionality of the endonuclease was demonstrated.

Establishment of Huntington

Disease iPSCs. After the groundbreaking discovery that primary somatic cells can be reprogrammed into induced pluripotent stem cells (iPSCs) by Yamanka's group, we have established a human HD patient-derived neural stem cell (NSC) model of HD to understand disease pathogenesis and to test disease relevant mechanisms in vitro and in vivo (13, 16).

In published studies, we developed isogenic corrected HD-iPSCs by using HR to replace the expanded CAG repeat with a normal repeat length (13). Our targeting strategy is shown in FIG. 1, panel A. We engineered homologous arms from a bacterial artificial chromosome (BAC) clone containing the entire HTT gene with normal CAG length (21 CAG). A removable cassette that contains a PGK-neo and the CMV-EGFP is incorporated at the 5' end of the upstream sequence. We nucleofected HD-iPSCs with the targeting vector and pEGFP controls (FIG. 1, panel B) and selected with G418. An initial screen for CAG contractions yielded 12/203 clones, which were positive (FIG. 1, panels C-F). We used Southern blot analysis to identify corrected clones. We found 2 clones (c-HD-iPSC-clone C127 and c-HD-iPSC-clone C116), which were correctly targeted for gene correction (FIG. 1, panel D). Western blots with 1C2 of the HD-iPSCs and corrected clones confirm the concordant loss of polyQ-expanded HTT protein (FIG. 1, panel E).

Corrected HD-iPSCs maintained pluripotent characteristics of the original HD-iPSC clones (13). For details see our published work (13). We also used the CRISPR/Cas9 to generate an isogenic allelic series (12), perform genetic correction (unpublished results) and have now applied our expertise to making isogenic iPSCs with ApoE $\epsilon2/\epsilon2$, $\epsilon3/\epsilon3$ and $\epsilon4/\epsilon4$ genotypes.

Database Searching, Design and Purification of Novel CNS Cell Penetrating Peptides.

We have validated one cell penetrating peptides for delivery into the brain. The CPP is unreported in the literature and is derived from the Zika virus. This peptide was designed by database searching and evaluation of the current structural data on the virus (FIG. 2). The Zika CPPs were attached to the Cas9 nickase (CPP-Cas9n) protein, which were then purified in milligram quantities (FIG. 3). We can use this methodology to select, clone and purify multiple novel CPPs of viral origin.

Delivery of CPP-CAS9 (PZ) into Neuronal Stem Cells for Genetic Correction.

To demonstrate that our purified proteins, CPP-Cas9n (PZ) are capable of translocating into neuronal cells we applied the CPP-Cas9n purified protein successfully on human neural stem cells (FIG. 4). It persists for over 72 hours but as would be expected if it eventually clears from the cells over time. The proteins were not toxic to the cells as there were no changes in cell morphology or growth during the treatments (data not shown). This data confirms that our protein enters the neural stem cells and remains intact after entering the cells. In addition we added our CPP-Cas9n proteins to a mouse striatal cell line and the human neuroblastoma SHSY5Y line and observed similar results. We can therefore expect that the novel CPPs should be usable across multiple relevant cell lines. To insure that the CPP-Cas9n we delivered was still active we transfected the NSCs with a myc-tagged donor and gRNA plasmids, then harvested the genomic DNA and used myc-tag specific primers to amplify the homologous repair site where the donor was integrated (FIG. 5). This method was done both with conjugation of the CPP-Cas9n to the gRNAs as an RNP and as NSCs transfected with both donor and gRNAs, having the CPP-Cas9n added after transfection.

Delivery of CPP-CasQ into Mice and Detection in Organs.

The Zika CPP-Cas9n protein was injected IV at 300 ug/injection for a two week time period, sacrificed and tissue homogenates were generated. As shown in western blot analysis using Cas9 antibody detects the protein in the liver and kidney (FIG. 6). Using immunoprecipitation the protein is readily detected in the brain. Further studies were done in which additional mice were injected with 300 ug of Zika CPP-Cas9n and perfused, their brain harvested and stained with a Flag-tag antibody which is present on the construct (FIG. 7). The Zika CPP-Cas9n shows a wide distribution throughout the brain, especially prominent in the hippocampus, striatum and cerebellum, both critical regions in neurodevelopmental and neurodegenerative diseases. The observation that a CPP derived from Zika, which is primarily a neuronal viruses, distributes to multiple organs outside the brain indicates that the CPPs we discover could target multiple organs. This is a very positive outcome as it will increase our ability to target multiple organs with one construct, which is relevant for many diseases.

Materials and Methods

Design and Sequence

The cell penetrating peptide amino acid sequence from Zika virus is ENLEYRIMLSVHGSQHSGMIVNDTG HETDENRAKVEITPNSPR (SEQ ID NO:1). This CPP was expressed using a DNA *E. coli* optimized sequence GAG AAT CTG GAA TAC CGT ATC ATG TTA AGC GTG CAT GGA TCA CAG CAT TCA GGA ATG ATT GTG AAC GAC ACA GGA CAT GAA ACT GAT GAA AAC CGC GCG AAA GTG GAA ATC ACT CCC AAC AGT CCC CGT (SEQ ID NO:37).

The Zika virus CPP peptide was placed in a protein construct that features the following: 6×His tag-Maltose Binding Protein-TEV site-Zika CPP-3X Flag Tag-NLS-HA-Cas9D10A-NLS (see, e.g., FIG. 3, panel A). This protein with the Zika cell penetrating peptide will from this point on be called "PZ". The sequence was synthesized as part of a gene block by IDT. It was then cloned into a pET His6 MBP TEV LIC cloning vector (1M) (Addgene Plasmid #29656). The Cas9D10A nickase from this plasmid pX335-U6-Chimeric_BB-CBh-hSpCas9n(D10A) (Addgene Plasmid #4233).

Expression and Purification:

The PZ construct was expressed in BL21 star *E. coli*. The protein was grown and expanded at 37° C. in 2×TY broth with Kanamycin. It was induced at 25° C. overnight with 0.5 uM IPTG. The *E. coli* was microfluidized or sonicated and the protein was purified over a Ni/NTA column (Invitrogen 60-0442) in a buffer of 20 mM Tris, 500 mM NaCl, pH 8.5. It was then eluted in 20 mM Tris, 500 mM NaCl, 300 mM Imidazole, pH 8.5. The eluted solution was then concentrated using a Millipore 100 kD concentrator, and then sterile filtered using a 45 μM syringe filter. It was stored in 20 mM Tris, 154 mM NaCl, 10% Glycerol pH 8.5.

Protein was analyzed for quality and purity by coomassie and western blot (FIG. 2B). It is assumed that approximately 50% of the eluted solution is full length PZ, with the remainder being fragments of PZ.

Testing the Cell Penetrating Ability:

In Cells:

In SHSYSY, striatal cells or human NSCs: cells were grown to 75% confluency in DMEM+10% FBS in a six well plate. A total of 20 ug of PZ sterilized solution is added directly onto cells. The cells were harvested by rinsing 2× with DBPS (Corning 21031CV), scrapping, spinning down the cell pellet and rinsing the pellet 2× more with DPBS. The pellet was then lysed with MPER and 1× protease inhibitor (Roche). Total cell lysate protein was quantified by a BCA assay, and 30 ug of this lysate was added to a western blot. Western blots ere probed with Cas9 antibody (1:1000, Cell signaling 14697S), and secondary of anti-mouse (1:2500 GE Healthcare NXA931).

In NSCs the process was repeated but with growth conditions optimized for NSC culture.

When testing the ability for recombination in NSCs the cells were transfected with DNA-In at the optimized amount for both DNA-In and our Donor and gRNA plasmids. The following day the media was changed and the PZ protein was added at 10 ug per 6 well in a 6 well plate. Cells were grown for another 48 hours, with a media change and then harvested. Cells were extensively rinsed with DPBS (Corning 21031CV) before harvest to remove residual PZ protein.

For the RNP (Ribonucleoprotein) the PZ was conjugated to the gRNA that were provided and prepared by Synthego according to the manufacturers recommended amounts. Each well had bug of PZ protein conjugated to the manufacturers recommended gRNA amount. The RNPs were added twice during the experiments at 48 hours pre-harvest and 24 hours pre-harvest. Cells were harvested as described above, and lysates were obtained as stated above.

In Mice:

A total of 500 µg protein solution was delivered to 8-10 week old C57Bl/6 female mice by interperiotneal (IP), subcutaneous (SC), or intravenous (IV) injections three times over a one week period. A group of No Treatment mice and a group of "Saline" mice were also done for each type of injection method. A second cohort of mice YAC128 (HD) females was injected for three weeks twice a week at 300 ug/injection as IV (tail vein) injections. Organs (brain, lungs, heart, liver, kidney, spleen) and blood were harvested four hours post final injection. Organs were homogenized in 600 ul of TPER with protease inhibitor lacking EDTA (Roche 11873580001). The homogenized lysates were run on a 4-12% Bis-Tris gel in MES buffer (Life Technologies NP0002) with antioxidant (Invitrogen NP0005) at 200V for 60 minutes. Transfer was done overnight in Transfer Solution (Life Technologies NP0006-1) at 20V for 840 minutes onto a nitrocellulose membrane. Membranes were blocked with 5% milk in TBST and then probed with a variety of antibodies at 1:100 (Cell Signaling Cas9 14697S, New England Biolabs MBP E8032S, Covance/BioLegend HA.11 901501, at 1:1000 Cell Signaling beta-actin 4967S, at 1:1000 Sigma Aldrich alpha-tubulin T6199. For secondary either anti-mouse (GE Healthcare NXA931) or anti-rabbit (GE Healthcare NA934) was used at 1:2500. When necessary immunoprecipitation on Ni/NTA beads was used to purify the protein from the homogenized organ lysate.

Results.

In Cells.

In the cell lines (SHSY5Y, NSCs, and mouse striatal cells) the results are essentially the same. An amount of 10-20 µg of protein was added to the cells. The cells were rinsed and harvested 24 hours later, they were lysed and the total protein amount was quantified. The full length PZ protein was found present to varying degrees in all of the above cells types, most prominently in the neuronal cells types of SHSY5Y, mouse striatal cells and human neuronal stem cells (NSCs).

In Mice

The PZ protein was detectable in western blot assays from homogenized kidney and liver lysates without the assistance of immunoprecipitation. For the brain it was necessary to use immunoprecipitation on Ni/NTA beads targeting the 6×His tag on the PZ protein, the protein was detected on western blots using the elutes from the immunoprecipitation. No PZ protein bands were detected in the No Treatment or Saline control mice. These results were consistently replicated over a total of eight different mice.

IHC: YAC128 female mice were IV injected with either a saline solution or 300 ug of PZ over a two week time period, three times a week. Mice were harvested four hours post final injection. The mice were perfused with 4% PFA. Organs were harvested and embedded in paraffin, sectioned and stained with Sigma Flag Tag (F7425) at 1:100, secondary was anti-rabbit Alexa 555 (Invitrogen A21428). Slides were mounted with prolong gold with Dapi (Invitrogen P36931).

REFERENCES

1) Sirohi et al. (2016) *Science* DOI: 10.1126/science.aaf5316 (specifically see supplemental data).
2) Smit et al. (2011) Viruses, 3(2): 160-171.
3) Tang et al. (2016) Cell Stem Cell, 18(5): 587-590.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

---

What is claimed is:

1. A construct comprising a cell penetrating peptide attached to an effector that is to be delivered into a cell, wherein:
said cell penetrating peptide comprises a Zika cell penetrating peptide (Zika CPP) where the amino acid sequence of said cell penetrating peptide comprises the sequence ENLEYRIMLSVHGSQHSGMIVNDTG HETDENRAKVEITPNSPR (SEQ ID NO:1), or a fragment thereof that retains the ability to penetrate into a target cell, and said cell penetrating peptide ranges in length up to 50 amino acids; and
said effector is selected from the group consisting of a protein that is not a Zika protein, a nucleic acid, an organic compound, a viral particle, and a nanoparticle.

2. The construct of claim 1, wherein the amino acid sequence of said cell penetrating peptide consists of the sequence ENLEYRIMLSVHGSQHSGMIVNDTG HETDENRAKVEITPNSPR (SEQ ID NO:1), or a fragment thereof that retains the ability to penetrate into a target cell.

3. The construct of claim 1, wherein said cell penetrating peptide is attached to said effector by a non-covalent interaction.

4. The construct of claim 3, wherein said non-covalent interaction comprises a biotin/avidin interaction.

5. The construct of claim 1, wherein said cell penetrating peptide is chemically conjugated to said effector.

6. The construct of claim 5, wherein said cell penetrating peptide is chemically conjugated to said effector via a non-cleavable linker or via a cleavable linker.

7. The construct of claim 6, wherein:
said cell penetrating peptide is chemically conjugated to said effector via a cleavable linker comprising a disulfide linker or an acid-labile linker; or
said cell penetrating peptide is chemically conjugated to said effector via an acid-labile linker comprising a moiety selected from the group consisting of a hydrazone, an acetal, a cis-aconitate amide, and a silyl ether.

8. The construct of claim 1, wherein said effector comprises a polypeptide and said construct comprises a fusion protein, wherein:
said fusion protein comprises said cell penetrating peptide directly attached to said effector; or
said fusion protein comprises said cell penetrating peptide attached to said effector by an amino acid; or
said fusion protein comprises said cell penetrating peptide attached to said effector by a peptide linker.

9. The construct of claim 8, wherein:
said fusion protein comprises said cell penetrating peptide attached to said effector by a peptide linker and said linker comprises an amino acid sequence cleavable by a protease; or
said fusion protein comprises said cell penetrating peptide attached to said effector by a peptide linker and said linker comprises an amino acid sequence cleavable by a cathepsin; or
said fusion protein comprises said cell penetrating peptide attached to said effector by a peptide linker wherein said peptide linker comprises a dipeptide valine-citrulline (Val-Cit), or Phe-Lys; or
said fusion protein comprises said cell penetrating peptide attached to said effector by an amino acid or peptide linker selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, GGGG (SEQ ID NO:22), PSGSP (SEQ ID NO:23), PSPSP (SEQ ID NO:24), KKKK (SEQ ID NO:25), RRRR (SEQ ID NO:26), ASASA (SEQ ID NO:27), GGSGGS (SEQ ID NO:28), GGGGS (SEQ ID NO:29), GGGGS GGGGS (SEQ ID NO:30), GGGGS GGGGS GGGGS (SEQ ID NO:31), GGGGS GGGGS GGGGS GGGGS (SEQ ID NO:32), GGGGS GGGGS GGGGS GGGGS GGGGS (SEQ ID NO:33), GGGGS GGGGS GGGGS GGGGS GGGGS GGGGS (SEQ ID NO:34), GGGGS GGGGS GGGGS FK GGGGS GGGGS GGGGS (SEQ ID NO:35), and GGGGS GGGGS GGGGS VA GGGGS GGGGS GGGGS (SEQ ID NO:36).

10. The construct of claim 1, wherein said effector comprises a targeted endonuclease.

11. The construct of claim 10, wherein said targeted endonuclease comprises a class 2 CRISPR/Cas endonuclease.

12. The construct of claim 11, wherein said class 2 CRISPR/Cas endonuclease is a type II CRISPR/Cas endonuclease or a type V or type VI CRISPR/Cas endonuclease.

13. The construct of claim 12, wherein the class 2 CRISPR/Cas endonuclease comprises a Cas9 protein selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

14. The construct of claim 13, wherein said Cas9 protein is a Cas9 protein fused to a repressor or an activator domain.

15. The construct of claim 14, wherein said Cas9 protein is fused to a VP64 transcriptional activator or to a VP16 transcriptional activator, or to a repressor domain comprising a Krüppel associated box (KRAB) domain.

16. The construct of claim 12, wherein the class 2 CRISPR/Cas protein is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

17. The construct of claim 10, wherein said targeted endonuclease is complexed with a guide RNA to form a ribonucleoprotein complex.

18. The construct of claim 17, wherein:
said guide RNA comprises one or more locked nucleic acids (LNAs); or
said guide RNA comprises one or more bridged nucleic acids; and/or
said guide RNA comprises one or more bridged nucleic acids, wherein said bridged nucleic acids comprise one or more N-methyl substituted BNAs (2',4'-BNA$^{NC}$).

19. The method of claim 17, wherein said guide RNA (gRNA) targets a gene selected from the group consisting of HTT, AADC, TH, GCH-1, SOD1, PGC-la, UBE3A, NECO2, and SNRPN.

20. The construct of claim 10, wherein said targeted endonuclease comprises a zinc finger protein or a TALEN.

21. The construct of claim 1, wherein said effector comprises a viral particle.

22. The construct of claim 1, wherein said effector comprises a nucleic acid.

23. The construct of claim 22, wherein said effector comprises a nucleic acid selected from the group consisting of a DNA, an RNA, an siRNA, an antisense oligonucleotide, a transposon, and a guide RNA (gRNA).

24. A method of delivering an effector into a cell, said method comprising contacting said cell with a construct of claim 1.

25. The construct of claim 1, wherein the amino acid sequence of said cell penetrating peptide consists of the sequence ENLEYRIMLSVHGSQHSGMIVNDTG HETDENRAKVEITPNSPR (SEQ ID NO:1).

* * * * *